(12) United States Patent
Nagar

(10) Patent No.: US 11,992,459 B2
(45) Date of Patent: May 28, 2024

(54) DEVICES, SYSTEMS AND METHODS FOR CONTROLLING ENVIRONMENTAL CONDITIONS OF SUBSTANCES

(71) Applicant: Ron Nagar, Tel-Aviv (IL)

(72) Inventor: Ron Nagar, Tel-Aviv (IL)

( * ) Notice: Subject to any disclaimer, the term of this patent is extended or adjusted under 35 U.S.C. 154(b) by 187 days.

(21) Appl. No.: 15/778,110

(22) PCT Filed: Nov. 23, 2016

(86) PCT No.: PCT/IL2016/000021
§ 371 (c)(1),
(2) Date: May 22, 2018

(87) PCT Pub. No.: WO2017/090019
PCT Pub. Date: Jun. 1, 2017

(65) Prior Publication Data
US 2018/0333330 A1    Nov. 22, 2018

Related U.S. Application Data

(60) Provisional application No. 62/367,648, filed on Jul. 28, 2016, provisional application No. 62/317,578,
(Continued)

(51) Int. Cl.
*F25D 3/08* (2006.01)
*A61J 1/14* (2023.01)
(Continued)

(52) U.S. Cl.
CPC .............. *A61J 1/165* (2013.01); *A61J 1/1468* (2015.05); *A61M 5/002* (2013.01);
(Continued)

(58) Field of Classification Search
CPC .. B61D 81/38; A61J 1/165; F25D 3/00; F25D 3/02; F25D 3/06; F25D 3/08; F25D 3/107; F28D 20/02; F28D 20/028
See application file for complete search history.

(56) References Cited

U.S. PATENT DOCUMENTS 3,802,220 A   4/1974  Pompo
4,373,535 A   2/1983  Martell
(Continued)

FOREIGN PATENT DOCUMENTS

CN    101208568 A   6/2008
CN    108027192 A   5/2018
(Continued)

OTHER PUBLICATIONS

Extended European Search Report dated Jul. 2, 2019 for EP Application No. 16868134.4, 7 pages.
(Continued)

*Primary Examiner* — Jerry-Daryl Fletcher
*Assistant Examiner* — Daniel C Comings
(74) *Attorney, Agent, or Firm* — COOLEY LLP

(57) ABSTRACT

An apparatus, comprising an environmental control element configured to control at least one environmental condition of a substance contained within a chamber, the environmental control element includes a thermal insulator configured to provide a thermal shield to the substance and a phase change material (PCM) configured to thermally regulate at least one environmental condition. The environmental control element is configured to control the environmental condition without use of an external power source, and the PCM is configured to return to its solid phase without user intervention.

22 Claims, 27 Drawing Sheets

Related U.S. Application Data filed on Apr. 3, 2016, provisional application No. 62/299,573, filed on Feb. 25, 2016, provisional application No. 62/289,381, filed on Feb. 1, 2016, provisional application No. 62/269,993, filed on Dec. 20, 2015, provisional application No. 62/258,556, filed on Nov. 23, 2015.

(51) Int. Cl.
| | |
|---|---|
| *A61J 1/16* | (2023.01) |
| *A61M 5/00* | (2006.01) |
| *A61M 5/168* | (2006.01) |
| *A61M 5/24* | (2006.01) |
| *A61M 5/44* | (2006.01) |
| *A61M 5/142* | (2006.01) |

(52) U.S. Cl.
CPC .......... *A61M 5/16804* (2013.01); *A61M 5/24* (2013.01); *A61M 5/44* (2013.01); *F25D 3/08* (2013.01); *A61J 2200/42* (2013.01); *A61J 2200/44* (2013.01); *A61J 2200/50* (2013.01); *A61J 2200/72* (2013.01); *A61M 5/142* (2013.01); *A61M 5/445* (2013.01); *A61M 2205/13* (2013.01); *A61M 2205/3306* (2013.01); *A61M 2205/3368* (2013.01); *A61M 2205/3375* (2013.01); *A61M 2205/3561* (2013.01); *A61M 2205/3606* (2013.01); *A61M 2205/3633* (2013.01); *A61M 2205/364* (2013.01); *A61M 2205/3646* (2013.01); *A61M 2205/3653* (2013.01); *A61M 2205/502* (2013.01); *A61M 2205/6045* (2013.01); *A61M 2205/6054* (2013.01); *A61M 2205/6063* (2013.01); *A61M 2205/8206* (2013.01); *F25D 2303/083* (2013.01); *F25D 2400/36* (2013.01)

(56) References Cited

U.S. PATENT DOCUMENTS

| | | | | |
|---|---|---|---|---|
| 4,723,974 | A * | 2/1988 | Ammerman | A01N 1/0273 |
| | | | | 62/530 |
| 4,924,935 | A | 5/1990 | Van Winckel | |
| 5,695,090 | A | 12/1997 | Burdick | |
| 6,454,746 | B1 | 9/2002 | Bydlon et al. | |
| 7,861,538 | B2 † | 1/2011 | Welle | |
| 8,061,149 | B1 * | 11/2011 | Gowans | A61J 1/165 |
| | | | | 62/3.62 |
| 8,398,602 | B2 † | 3/2013 | Lio | |
| 8,646,282 | B2 † | 2/2014 | Ilercil | |
| 8,663,167 | B2 | 3/2014 | Bartha | |
| 8,887,512 | B2 † | 11/2014 | Olsen | |
| 9,447,995 | B2 † | 9/2016 | Bloedow | |
| 9,791,184 | B2 † | 10/2017 | Novisoff | |
| 10,254,499 | B1 | 4/2019 | Cohen et al. | |
| 2002/0000443 | A1 * | 1/2002 | Hunter | F25D 3/125 |
| | | | | 220/592.26 |
| 2006/0191282 | A1 * | 8/2006 | Sekiya | B65D 81/3823 |
| | | | | 62/457.2 |
| 2006/0271014 | A1 | 11/2006 | Hynes et al. | |
| 2006/0276768 | A1 | 12/2006 | Miller et al. | |
| 2008/0022696 | A1 | 1/2008 | Welle et al. | |
| 2008/0264261 | A1 | 10/2008 | Kavazov et al. | |
| 2008/0269687 | A1 | 10/2008 | Chong et al. | |
| 2009/0049845 | A1 | 2/2009 | McStravick et al. | |
| 2009/0139248 | A1 | 6/2009 | Crumlin et al. | |
| 2010/0314397 | A1 * | 12/2010 | Williams | B65D 81/3823 |
| | | | | 220/592.01 |
| 2011/0155621 | A1 | 6/2011 | Lindquist et al. | |
| 2011/0218502 | A1 | 9/2011 | Iio et al. | |
| 2012/0312031 | A1 | 12/2012 | Olsen | |
| 2013/0221013 | A1 | 8/2013 | Kolowich | |
| 2013/0255306 | A1 | 10/2013 | Mayer | |
| 2014/0090737 | A1 | 4/2014 | Reid | |
| 2014/0165607 | A1 † | 6/2014 | Alexander | |
| 2014/0216485 | A1 | 8/2014 | Egoyants et al. | |
| 2014/0343493 | A1 | 11/2014 | Wengreen | |
| 2015/0151893 | A1 * | 6/2015 | Wengreen | B65D 81/383 |
| | | | | 62/457.2 |
| 2015/0229267 | A1 | 8/2015 | Hilliard | |
| 2017/0241702 | A1 | 8/2017 | Klett et al. | |
| 2018/0207368 | A1 | 7/2018 | Nagar | |
| 2018/0283761 | A1 | 10/2018 | Büttiker | |
| 2019/0285328 | A1 | 9/2019 | Emond et al. | |
| 2021/0396446 | A1 | 12/2021 | Nagar | |

FOREIGN PATENT DOCUMENTS

| | | | | |
|---|---|---|---|---|
| EP | 2361203 | A1 | 8/2011 | |
| GB | 2176711 | A | 1/1987 | |
| GB | 2422657 | A * | 8/2006 | ............. C09K 5/066 |
| JP | 02115672 | A | 4/1990 | |
| JP | 04201877 | A | 7/1992 | |
| WO | WO-2013/034458 | A1 | 3/2013 | |
| WO | WO-2014/064691 | A2 | 5/2014 | |
| WO | 2014192019 | A2 | 12/2014 | |
| WO | WO-2015/055836 | A1 | 4/2015 | |
| WO | WO-2016011207 | A1 | 1/2016 | |
| WO | WO-2017090019 | A2 | 6/2017 | |

OTHER PUBLICATIONS

International Search report for Application No. PCT/IL16/00021, dated May 16, 2017.
International Search Report and Written Opinion, dated Oct. 7, 2015, for International Application No. PCT/US2015/040655.
Screenshots from Website: www.insulinsafe.com/cn/en/category/product; Sep. 13, 2014; Beijing Insulinsafe Healthcare Limited.
Screenshots from Website: www.insulinsafe.com/cn/en/; May 10, 2013; Beijing Insulinsafe Healthcare Limited.
Extended European Search Report dated Feb. 21, 2018 for EP Application No. 15822617.5, 7 pages.
Extended European Search Report dated Nov. 20, 2019 for EP Application No. 19181060.5, 7 pages.
Extended European Search Report for Application No. EP20190875793, dated Oct. 14, 2022, 11 pages.
International Search Report issued in PCT/IB2019/059096, dated Feb. 4, 2020, 1-3.

\* cited by examiner
† cited by third party

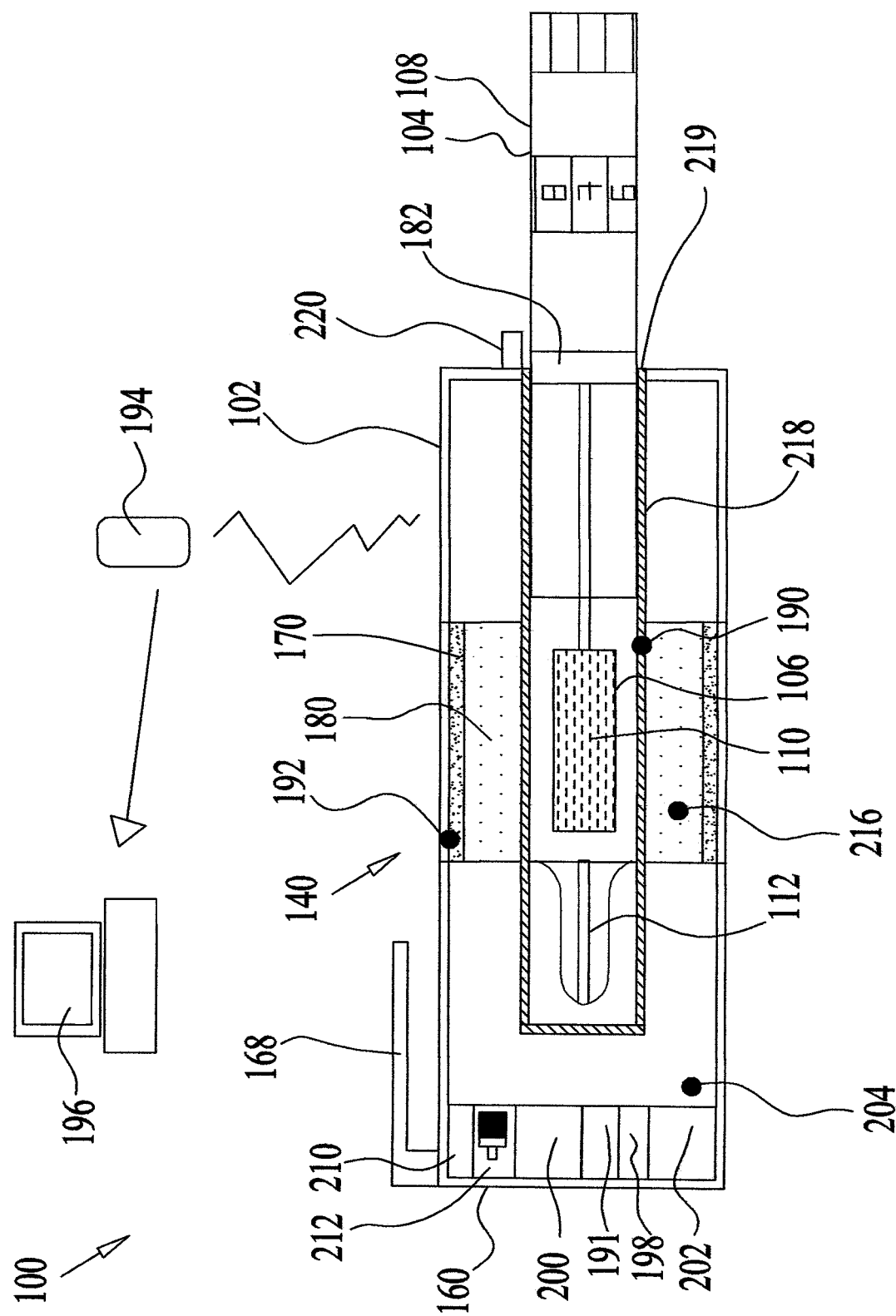

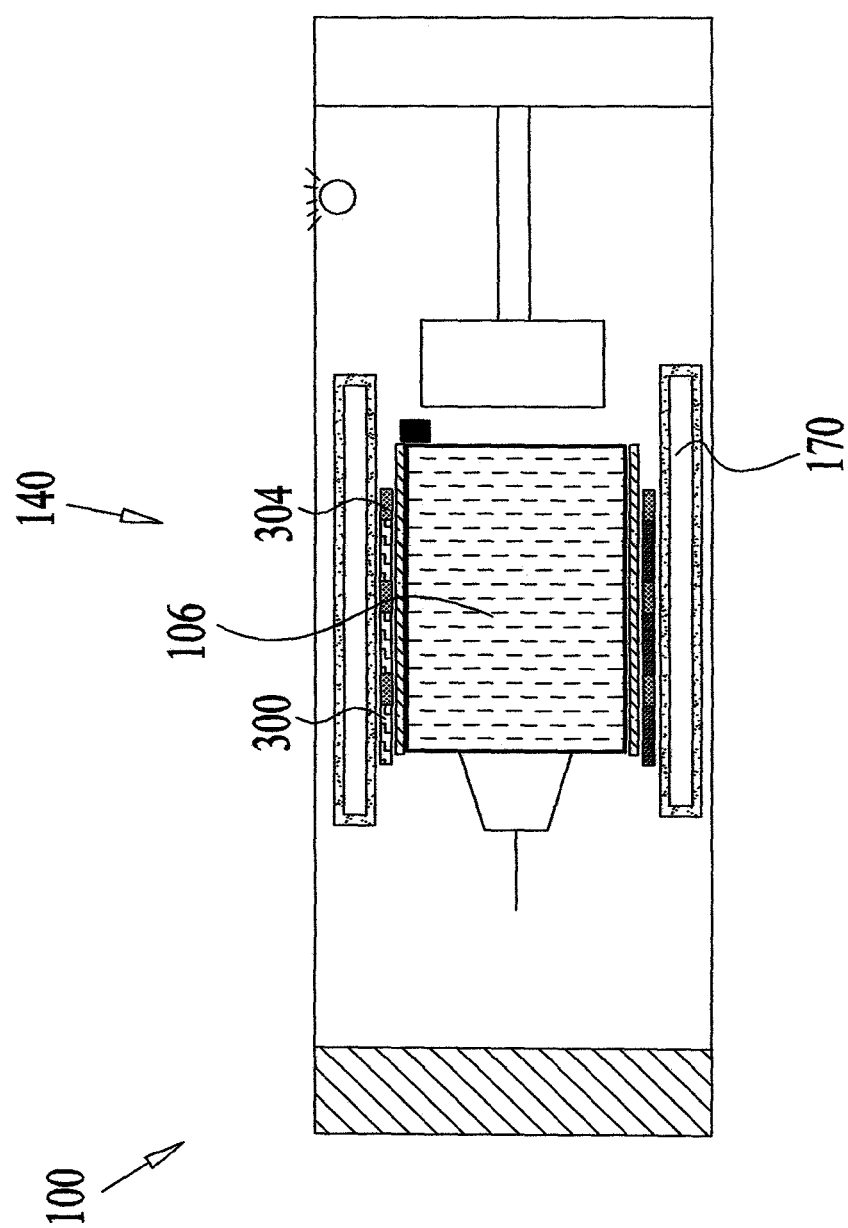

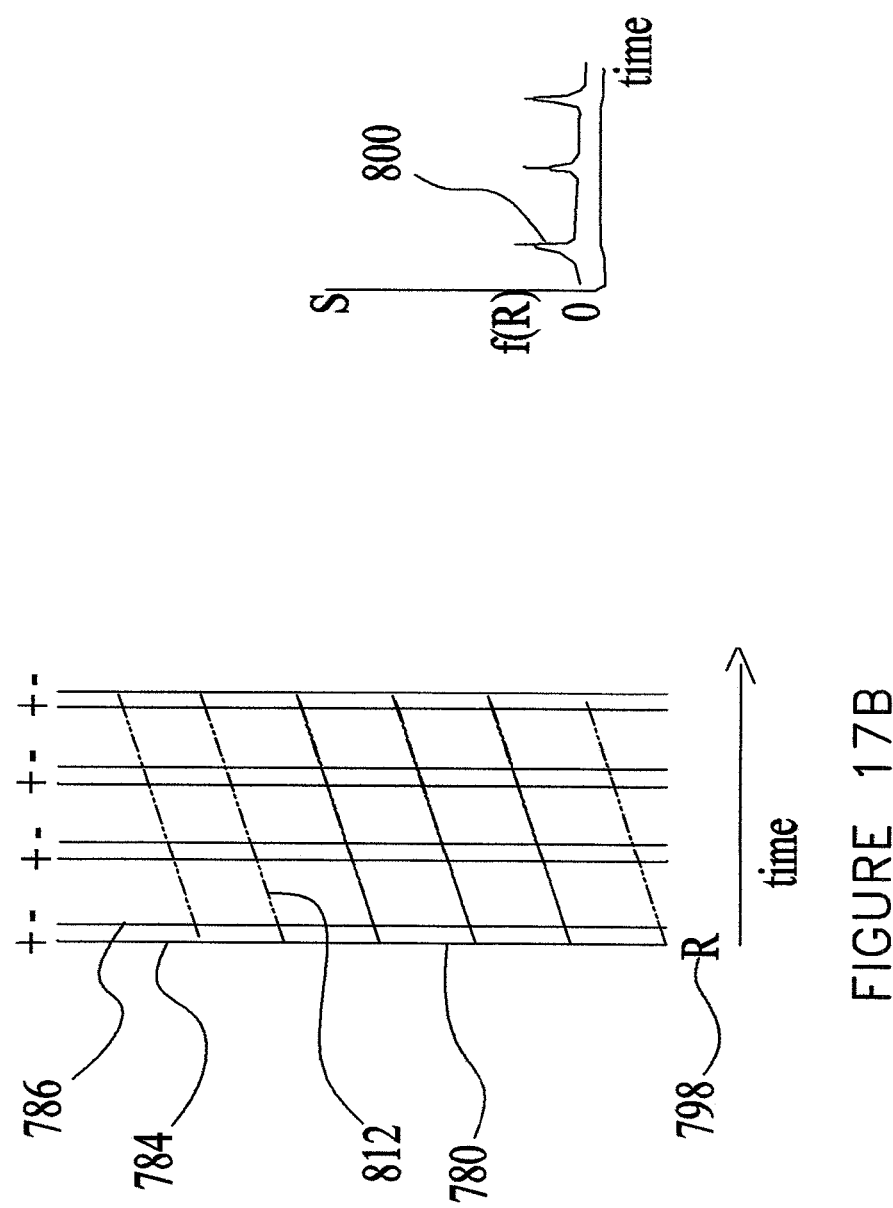

DEVICES, SYSTEMS AND METHODS FOR CONTROLLING ENVIRONMENTAL CONDITIONS OF SUBSTANCES

RELATED APPLICATIONS

This application is a 371 National Stage filing of PCT application no. PCT/IL2016/000021, having an international filing date of Nov. 23, 2016, which claims benefit of and priority to U.S. Provisional Patent Application Nos.:
- 62/258,556 filed Nov. 23, 2015, titled: "Devices Systems and Methods for Controlling and Maintaining Conditions of Substances";
- 62/269,993 filed Dec. 20, 2015, titled "Devices, Systems and Methods for Controlling and Maintaining Conditions of Substances";
- 62/289,381 filed Feb. 1, 2016, titled: "Devices Systems and Methods for Controlling Conditions of Substances";
- 62/299,573 filed Feb. 25, 2016, titled: "Devices, Systems and Methods for Controlling Conditions of Substances";
- 62/317,578 filed Apr. 3, 2016, titled: "Substance Delivery Device"; and
- 62/367,648 filed Jul. 28, 2016, titled: "Devices, Systems and Methods for Controlling and Maintaining Conditions of Substances".

Each of the foregoing disclosures are herein incorporated by reference in their entirety.

TECHNICAL FIELD

Some embodiments of the present disclosure generally relate to the targeted controlling of substance environmental conditions.

BACKGROUND

Drugs and other substances can be sensitive to environmental conditions such as light, humidity, temperature, atmosphere, pressure and other conditions. Many drugs and other substances have limited boundaries to such conditions that if exceeded, can degrade the drug efficacy or degrade the substance.

While apparatuses exist that can maintain drugs and substance containers, such as drug-containing delivery devices, under controlled environmental conditions, such current apparatuses are quite large and typically require a regular AC power supply for their operation, or large batteries of limited duration. Other devices, such as cooling packs, require large amounts of cooling material (ice or water evaporation) to maintain a case under cooled temperatures.

Additionally, these cooling packs do not provide means for assessing the remaining cooling material or cooling ability in the apparatus. Moreover, these cooling packs do not provide means for measuring the amount of substance remaining in the substance container to be controlled by the apparatus. Additionally, these cooling packs are not provided in compact shapes which can be directly mounted on the substance or drug container.

SUMMARY OF SOME OF THE EMBODIMENTS

In some embodiments of the present disclosure, the environmental conditions of any substance may be controlled. The environmental condition (which may be referred to as "condition" herein) may include light, humidity, temperature, atmosphere, pressure and other conditions. The substance may comprise in a non-limiting example, a drug, a biological substance, such as hormones, a growth hormone, blood, body fluids, sperms, or eggs. The substance may comprise cosmetics, such as lipsticks, perfumes, toiletries, hair or skin care products, sprays, mousses, emulsions and gels, for example. The substance may comprise, resins, adhesives, glues, epoxy or cyanoacrylate glue. The substance may include any suitable form, such as a solid, liquid, emulsion, gas, gel, granules, and powder or a combination thereof, for example. The substance may include more than one substance at the same or different state, such as, for example, a liquid mixed with another liquid or a liquid mixed with a powder. In some embodiments, keeping one component of the mixture at a particular environmental condition requires a smaller amount of power than both components. For example, a substance in powder state is of smaller volume than the same substance in liquid state. Therefore maintaining a small amount of powder at a specific temperature requires less power than maintaining a larger amount of liquid at the specific temperature.

In some embodiments, there is provided an apparatus including means to control the environmental conditions of a substance contained in a container. The apparatus may comprise an enclosure that includes at least one of the following elements: an insulating chamber (such as vacuum insulation—e.g. thermal insulation comprising INSULON® or similar constructed material, or any other form of thermal insulation) and an energy absorbing material (such as a phase change material (PCM)) to effect the environmental condition.

In some embodiments, the apparatus may further include means to detect the condition (such as temperature) of the substance as well as the condition of the ambient environment out of the enclosure. For example, the apparatus may include a temperature sensor configured for detecting the temperature of the substance in the substance container and a temperature sensor detecting the ambient temperature.

In some embodiments, there may be provided a visual display which can convey to the user information relating to the status of the substance and/or the apparatus, such as, inter alia, how much control capacity of the conditions remains within the apparatus; when was the substance used last or time passed from last use of the substance, and any information relating to the volume or amount of substance in the substance container.

In some embodiments, the apparatus may comprise a battery or other power source and electronics which may include a timer and a controller. In some embodiments the apparatus may include a wireless transponder (transmitter and receiver) Bluetooth, NFC or any other communication means. Communication may be to a cloud based App or to a database or any other data storage and/or processing machine.

There is provided according to some embodiments, an apparatus, comprising an environmental control element configured to control at least one environmental condition of a substance contained within a chamber, the environmental control element including a thermal insulator configured to provide a thermal shield to the substance and a phase change material (PCM) configured to thermally regulate at least one environmental condition. The environmental control element is configured to control the at least one environmental condition without use of external power source, thereby allowing the apparatus to be thermally self-recharging.

In some embodiments, the apparatus further comprises an enclosure shaped and sized so as to receive the chamber. In some embodiments, the apparatus is handheld and portable. In some embodiments, the substance comprises a drug having a maximal temperature efficacy limit, a phase change temperature of the PCM is selected to be equal or slightly less (e.g. by 0.5° C., or by about 1° C., or by about 2° C. or by about 3° C., or by about 4° C., or by about 5° C. less) than the drug maximal temperature efficacy limit.

In some embodiments, a volume of the PCM exceeds the volume of the chamber. In some embodiments, a volume of the PCM is about twofold or larger (or about threefold or more or in a range between twofold or about threefold larger, for example) than the volume of the substance chamber. In some embodiments, the thermal insulator comprises an insulating enclosure formed of two oppositely facing walls and an evacuated gap defined in between the walls. In some embodiments, the thermal insulator is formed of two mutually insertable inner and outer insulating enclosures.

In some embodiments, the PCM is positioned intermediate the inner and outer insulating enclosures. In some embodiments, the PCM is positioned intermediate the thermal insulator and the chamber. In some embodiments, the apparatus, further comprises thermally conductive elements provided for improving a uniform temperature distribution over a volume of the PCM and/or that of the substance. In some embodiments, the environmental control element is arranged in a vicinity of the chamber so as to provide control of the at least one environmental condition only to the chamber.

In some embodiments, the container comprises a pump and the delivery of the substance is by infusion. In some embodiments, the thermal insulation and optionally the PCM are configured to minimize pump occlusions.

In some embodiments, the apparatus further comprises a control capacity indicator configured to display a remaining environmental condition control capability provided by the PCM. In some embodiments, the PCM is configured to change from a first phase to a second phase, and the remaining environmental condition control capability display is based on a remaining amount of PCM in the first or second phase. In some embodiments, the PCM is configured to change from a solid phase to a liquid phase, and the remaining environmental condition control capability display is based on a remaining amount of PCM in the solid phase. In some embodiments, the control capacity indicator is configured to display a measure of time indicative of the remaining environmental condition control capability.

In some embodiments, the PCM layer includes at least two types of PCMs each characterized by a different phase change temperature. In some embodiments, at least two types of PCMs are mixed together. In some embodiments, each type of PCM is in layer form and a first type of PCM layer overlies a second type of PCM layer.

In some embodiments, the apparatus further comprises a heating element configured to rapidly heat the substance. In some embodiments, the heating element is configured to rapidly heat the substance from a temperature in the range of about 2-8° C. to a temperature of around 25° C. In some embodiments the rapid heating may be within 60 seconds or less. In some embodiments, the heating element is configured to rapidly heat the substance from a low storage temperature to a higher use temperature. In some embodiments, the heating element is configured to rapidly heat the substance while not exceeding a maximal temperature efficacy limit of the substance.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The principles and operations of the systems, apparatuses and methods according to some embodiments of the present disclosure may be better understood with reference to the drawings, and the following description. The drawings are given for illustrative purposes only and are not meant to be limiting.

FIG. 1 is a schematic illustration of an exemplary environmental condition control apparatus constructed and operative according to some embodiments of the present disclosure;

FIG. 7 is a schematic illustration of an exemplary environmental condition control apparatus constructed and operative according to some embodiments of the present disclosure;

FIG. 17B is a simplified schematic illustration of an electrical representation of the arrangement of the transducer of FIG. 17A.

DETAILED DESCRIPTION

Figure 2A:
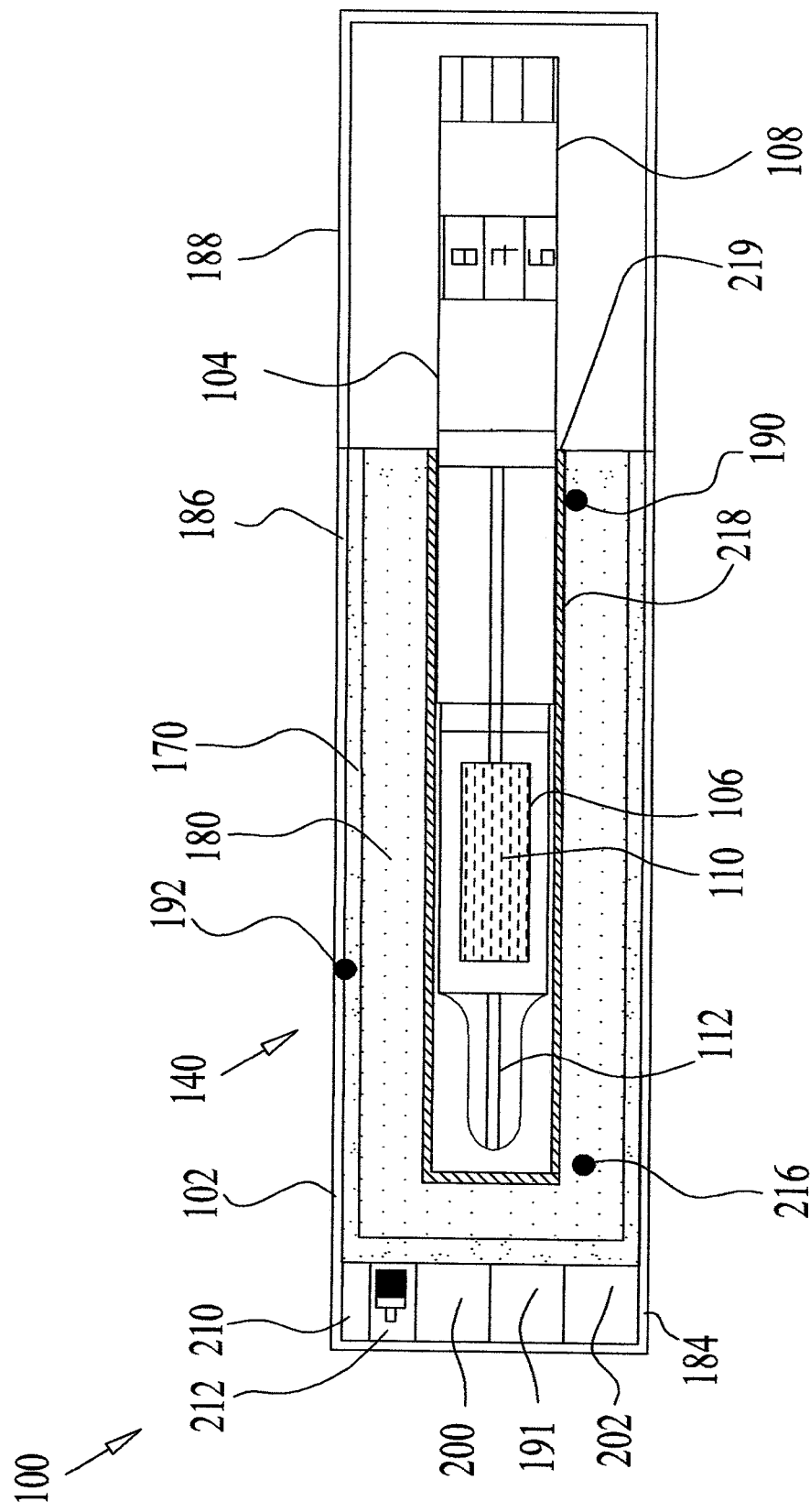
FIGS. 2A and 2B are each a schematic illustration of an exemplary environmental condition control apparatus constructed and operative according to some embodiments of the present disclosure.

FIGS. 1-6B each illustrate an exemplary environmental condition control apparatus 100 according to some embodiments of the present disclosure. The apparatus 100 may be sized to be handheld and portable. The apparatus 100 may be formed with an enclosure 102, which may comprise therein a volume for receiving a substance container 104 comprising a substance chamber 106 for storing a substance therein.

The substance may comprise in a non-limiting example, a drug, such as insulin, a protein based substance, such as a protein based drug, a biological substance, such as hormones, a growth hormone, blood, body fluids, sperms, or eggs. The substance may comprise cosmetics, such as lipsticks, perfumes, toiletries, hair or skin care products, sprays, mousses, emulsions or gels, for example. The substance may comprise, resins, adhesives, glues, epoxy or cyanoacrylate glue. The substance may be configured in any suitable form, such as a solid, liquid, emulsion, gas, gel, granules, or powder, for example. The substance may include more than one substance at the same or different phase, such as, for example, a liquid mixed with another liquid or a liquid mixed with a powder. Wherein the substance comprises a drug, the drug may include any suitable forms such as a solid, powder, tablet, pill, capsule, gas, gel, cream, emulsion, spray, a suppository or a combination thereof and may be delivered in any suitable manner.

In some embodiments, the container 104 may comprise a drug storage device or a drug delivery device, such as an injection pen 108 shown in FIG. 1. In some embodiments, the injection pen 108 may be a reusable injection pen configured for housing a replaceable drug cartridge comprising a drug 110, which is retained within the substance chamber 106 and injected via a needle 112. In some embodiments, the injection pen 108 may be a prefilled (or preloaded with a drug), disposable injection pen.

In some embodiments the container 104 may comprise an enclosure containing the substance chamber 106. In some embodiments, the container 104 may comprise a standalone container or may further reside in another substance delivery device. In some embodiments, the container 104, may comprise the entire substance delivery device, such as shown for example in FIG. 2A.

In a non-limiting example, the substance chamber 106 of the injection pen 108 or any other container 104 may comprise a drug reservoir and encompass a volume of few microliters up to 10 milliliters. In some embodiments the volume is up to about 1 milliliter. In some embodiments, the volume is about 10 milliliters or more than 10 milliliters. In some embodiments, the volume is less than 1 milliliter.

The container 104 may be configured in any suitable configuration for containing a substance therein. Some further exemplary containers 104 for containing drugs may include a syringe, a drug vial (e.g. the vial shown in FIG. 4), a drug cartridge (Shown in FIGS. 6A and 6B), an ampule, a pump, a pill box, or an inhalator.

The apparatus 100 may comprise an environmental control element 140 comprising an environmental control mechanism for controlling and/or regulating at least one environmental condition of the substance, including at least one of temperature, light, humidity, and pressure. The environmental control element 140 may be configured to maintain and/or change and/or regulate one or more such conditions of the substance to reach a predetermined selected condition. The environmental control element 140 may additionally be configured to monitor the environmental condition. The substance, such as drug 110, may be required to be stored and/or delivered at selected environmental conditions or at a range thereof.

Figure 5:
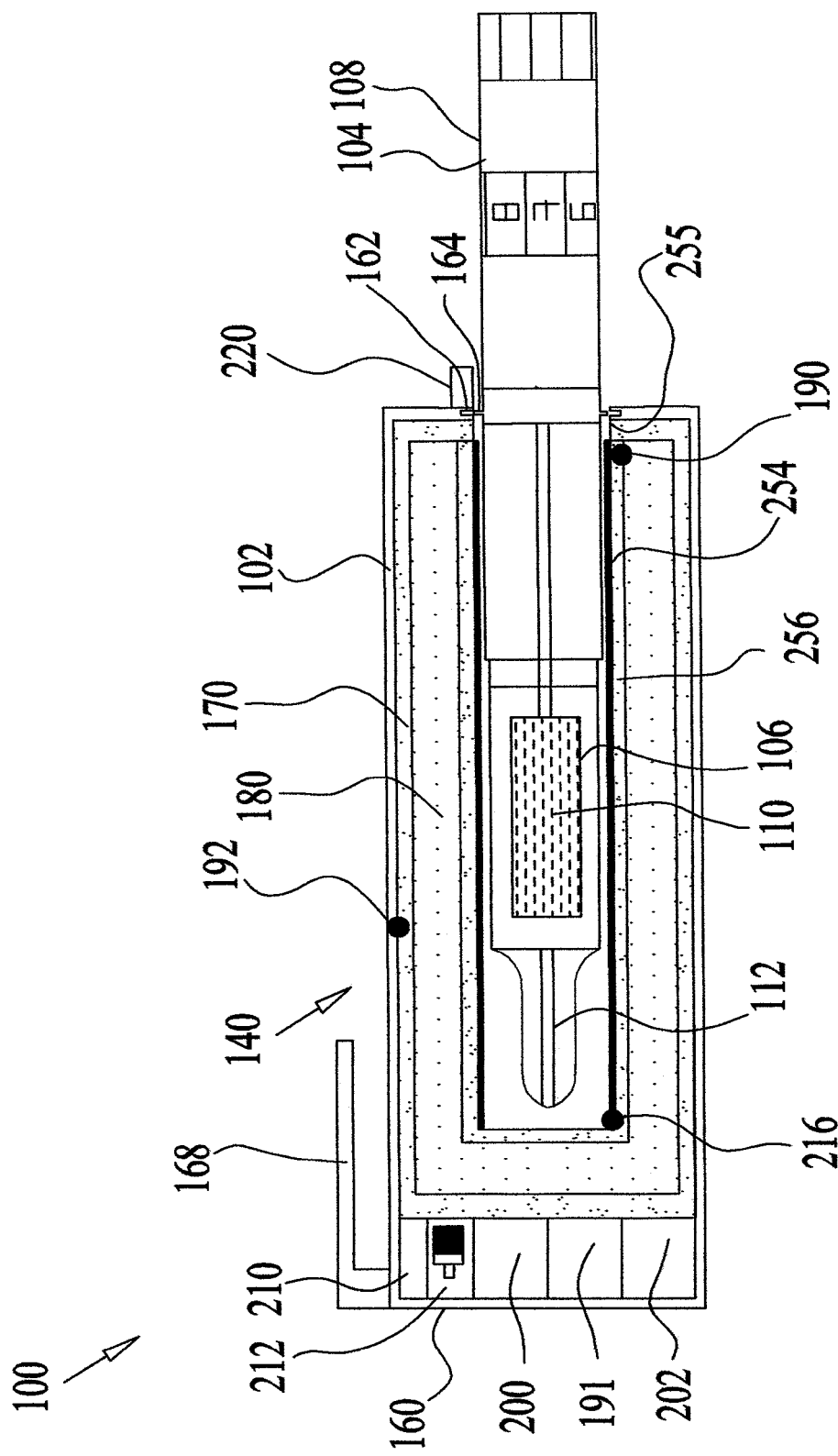
FIG. 5 is a schematic illustration of an exemplary environmental condition control apparatus constructed and operative according to some embodiments of the present disclosure.

The apparatus 100 may be formed in any suitable manner. In some embodiments, the apparatus 100 may be formed as a cylindrical cap 160 wherein the enclosure 102 comprises a cylindrical housing, as seen in FIG. 1. In some embodiments, the cap 160 (or any one of the apparatuses 100 described herein) may comprise mechanical features configured to fit the housing of the container 104, such as a recess 162 formed in the cap 160 configured to match a protrusion 164 protruding from the container 104 (or vice versa), as shown in FIG. 5.

The cap 160 may replace an original container cap or may be configured to be inserted over the original container cap. Cap 160 may be formed with a clip 168 for easily clasping the cap 160 along with the injection pen 108 to a pocket, handbag or any other object, for ease of portability.

The environmental control element 140 may comprise any suitable functionality for controlling and affecting one or more environmental conditions of the substance, such as drug 110. For example, wherein the condition is temperature, the environmental control element 140 may include temperature controlling elements for maintaining a desired temperature, and/or for heating and cooling. The environmental control element 140 may include passive control elements (e.g. as shown in FIGS. 1-4) and/or active control elements (e.g. as shown in FIG. 5).

A non-limiting example of a passive temperature controlling element includes thermal insulation 170 (which may be referred to as a "thermal insulator" interchangeably). The thermal insulation 170 may be placed intermediate the enclosure 102 and the chamber 106, for preventing uncontrolled changes in the substance temperature.

The thermal insulation 170 may be formed as a cylindrical layer at least partially underlying enclosure 102. The thermal insulation 170 may be formed in any suitable manner such as with evacuated portions, as will be described in reference to FIGS. 3A and 3B.

In some embodiments the control element 140 may comprise the thermal insulation 170 only. In some embodiments the control element 140 may comprise the PCM 180 only. In some embodiments the apparatus 100 may comprise both thermal insulation 170 and PCM 180.

In some embodiments, the apparatus 100 may comprise a phase change material (PCM) 180. The PCM may include a material with relatively high heat of fusion which, by melting and solidifying at a specific phase change temperature, is capable of absorbing, storing and releasing relatively large amounts of energy. The PCM 180 further absorbs heat flux which may pass through the thermal insulation 170 before it reaches the substance. The PCM is configured to effect control and regulation of the environmental condition of the substance contained in the container 104.

The PCM 180 may be configured in any suitable form, such as in layer form or microencapsulated form, for example. The PCM 180 is described herein as a "PCM layer" yet it is appreciated that this term also includes any suitable form of PCM.

The PCM layer 180 underlying, at least partially, the layer of the thermal insulation 170 may be formed with any suitable thickness or size. For example, few tens of grams of PCM (less than 100 grams) or a volume of anywhere in the range of 10-60 milliliters of PCM material can provide protection against environmental changes or maintain the substance, within the required environmental conditions (such as temperature) for a few hours, days, weeks, months or years.

In some embodiments, the apparatus 100 including the environmental control element 140 comprising thermal insulation 170 and PCM layer 180 which phase change transition temperature is adequately selected, may be thermally self-recharged due to the phase change capabilities of the PCM layer 180 and the thermal insulation 170 and the variations in ambient conditions which the apparatus is exposed to.

In some embodiments, the PCM layer 180 may overlie the thermal insulation 170, namely the PCM layer 180 may be positioned intermediate the thermal insulation 170 and the enclosure 102. In some embodiments the PCM layer 180 may be arranged within a thermal insulation construction, as will be described and shown in reference to FIG. 4.

In some embodiments, the overall volume of the PCM layer 180, in order to be effective, exceeds the volume of the substance chamber 106. (Though there are embodiments wherein the PCM layer volume is effective with an equal volume or smaller volume than the volume of the substance chamber 106). In some embodiments, the PCM volume may be, twofold or threefold larger or more than the substance chamber volume. In some embodiments, the PCM volume may be about twofold or less than the substance chamber volume. In some embodiments, the PCM volume may be in the range of about twofold to threefold larger than the substance chamber volume. In some embodiments, the PCM volume may be about more than threefold larger than the substance chamber volume. In a non-limiting example, a substance chamber may have a volume of about 1-10 cubic centimeters ("cc"), e.g. 3 cc. The PCM layer volume (or weight) contains about 10-100 grams or a volume of anywhere in the range of 10-60 milliliters of PCM material, in order to have an effective impact on the temperature change of the substance.

In some embodiments, the environmental control element 140 may be sized to surround the vicinity of the substance chamber 106 only, as seen in FIG. 1, where the thermal insulation 170 and PCM layer 180 are positioned in the vicinity of the chamber 106 only. It was found that surrounding substantially only the substance chamber 106 provides sufficient protection (namely control and/or regulation) of the substance from the ambient environment out of the enclosure 102. Namely, despite the exposed portion of the pen 108, the temperature of the substance was adequately controlled.

In other embodiments, the environmental control element 140 may be sized to surround more than just the vicinity of the substance chamber 106, such as also the needle region 112 and the plunger 182 region or any other region of the substance container 104.

According to some embodiments, the environmental control element 140 may comprise passive components, (e.g. not powered by an energy source) such as the thermal insulation 170 and PCM layer 180. Such an apparatus 100 including the environmental control element 140 comprising thermal insulation 170 and PCM layer 180 only, is thermally self-recharged due to the phase change capabilities of the PCM layer 180 and thermal insulation 170. The thermally self-recharged apparatus 100 does not require use of power, refrigeration or other means for controlling the environmental condition of the substance. This thermally self-recharging apparatus 100 may be used for a long time such as hours, weeks, months and even longer than a year without requiring user attention. The transition of the PCM 180 from a first phase to a second phase may be performed on its own, thereby self-regaining its thermal protection or regulation in response to ambient temperature variations. This self-regaining of thermal protection or thermal regulation may be achieved without supply of an additional or external power source (e.g. a source of power which is not the PCM 180 such as a battery or electrical power) and is referred to herein as "thermally self-recharging". The transition of the PCM 180 from a first phase to a second phase may include the transition from a liquid or partially liquid phase to a solid phase or vice versa.

A non-limiting example of a thermally self-recharged apparatus 100 may be provided by selecting the PCM transition temperature to be relatively slightly below the substance highest efficacy limit temperature while the selected temperature is above normal room temperature. In this case whenever the apparatus 100 is exposed to extreme temperatures exceeding the substance limit temperature the combination of the insulation 170 and PCM 180 will act to protect the substance from reaching its limit temperature, while when the ambient temperature returns to normal room temperature the PCM 180 will undergo phase transition back to its solid phase within some time.

In some embodiments, such as described in reference to FIGS. 1-4, the apparatus 100 may comprise a battery 200 and electronics 202 which are used not for controlling the substance, but rather for powering temperature sensors 190 and 192 and indicators 210 and 212, as will be further described. These electrical components may be obviated and even when provided in the apparatus 100, they require minimal power enabling the battery 200 to be used for a relatively long time. In a non-limiting example, the battery 200 may require minimal energy capabilities, such as less than about 500 mA/hours, or less than about 400 mA/hours, or less than about 300 mA/hours, or less than about 200 mA/hours, or less than about 100 mA/hours. The battery energy 200 may be sufficient to last more than a month or more than a few months of more than a year without requiring any recharging by an external power source. In some embodiments a primary (namely unrechargeable) battery 200 may be used or a rechargeable battery 200 may be used.

Turning to FIG. 2A, the control apparatus 140 is formed as a tube 184. The tube 184 may comprise a detachable first portion 186 and second portion 188 formed for insertion of container 104 (here shown as comprising a drug delivery device) therein and removal therefrom. The first portion 186 may be engaged with second portion 188 in any suitable manner, such as by a threaded engagement or a snap-fit engagement, for example.

Figure 2B:
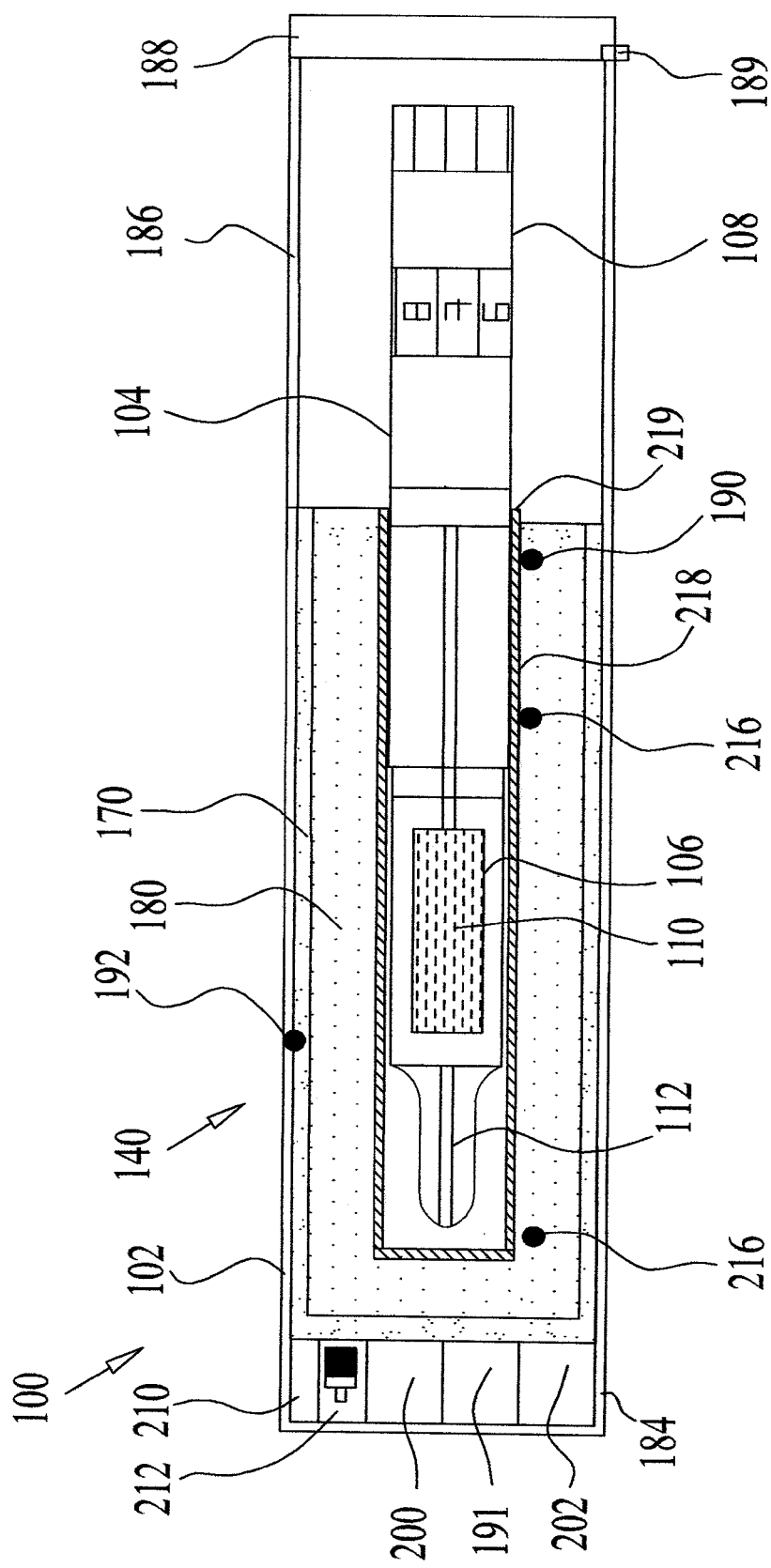

As seen in FIG. 2B, the tube 184 may comprise an elongated first portion 186 completely or partially overlying the injection pen 108. The second portion 188 may be formed at an edge of the tube 184. The second portion 188 may comprise a hinge 189 for pivoting the second portion 188 about first portion 186 for insertion of container 104 therein and removal therefrom.

The tube 184 may comprise a cylindrical layer of thermal insulation 170 in any suitable form. The PCM layer 180 may underlie the thermal insulation layer 170 such that it is positioned intermediate the thermal insulation 170 and the container 104. As shown in FIGS. 2A and 2B, the thermal insulation layer 170 and the PCM layer 180 may partially cover the injection pen 108.

The environmental control element 140 and/or the container 104 may include at least one or more temperature sensitive elements comprising substance temperature sensors 190, designed to monitor the temperature of the chamber 106. In some embodiments, the chamber 106 may be made of a material that is thermally conducting, such that the temperature of the chamber 106 is substantially similar to the temperature of the substance inside the chamber 106. In some embodiments data from the substance temperature sensors 190, is used by a controller 191 to determine if the device containing the substance was removed for use and placed back into the container 104.

An additional ambient temperature sensor 192 or a plurality of sensors 192 may be provided to monitor the ambient temperature outside the apparatus 100. In some embodiments, the ambient temperature sensor 192 may be placed in proximity to the enclosure 102. In some embodiments, the ambient temperature sensor 192 may be placed remotely from the apparatus 100 and may be in communication therewith. The ambient temperature sensor 192 and/or substance temperature sensor 190 may be configured to communicate with a tracking device or communication device 194 (FIG. 1) and/or a central database 196 via a wireless transponder or any other suitable communication means 198. In some embodiments, data from the substance temperature sensors 190, and ambient temperature sensor 192, is used by the controller 191 to determine if the container 104 was removed for use or if placed in the apparatus 100.

In some embodiments, the wireless communication having a limited range can be employed by a controller of the communication device 194, which may be a remote device, to detect the movement of the apparatus 100 away from the remote device 194 and further set out of signal range.

In a non-limiting example, the substance temperature sensor 190 and/or ambient temperature sensor 192 may comprise a thermistor.

In an exemplary, non-limiting embodiment, a thermoelectric generator chip may be positioned at one side thereof adjacent to chamber 106 for operating as the substance temperature sensor 190, while the opposite side can be used to detect the temperature external to the enclosure 102, thereby operating as the ambient temperature sensor 192. In some embodiments, the substance temperature sensor 190 may be physically disconnected from the substance chamber 106 and may communicate therewith contactlessly, such as with an infrared sensor, for example.

The apparatus 100 may comprise a power source, such as a battery 200 positioned at any suitable location. The apparatus 100 may comprise a controller 191 and electronics 202, such as a thermistor, a transistor, boards, wires or circuitry and/or a control circuit for controlling electrical components of the apparatus 100. Electrical connections (not shown) between the battery 200, and the controller 191, electronics 202 and any other electrical component, may be provided.

In some embodiments, the apparatus 100 may comprise additional components 204, such as additional sensors. Exemplary additional sensors may include capacitive sensors and accelerometer sensors which may be employed to detect touch of the apparatus 100 or removal of the container 104 from the apparatus 100 thereby detecting use of the container 104, such as delivery of the drug 110. The additional components 204 may comprise a memory device, and a timer, for example.

In some embodiments, the additional components 204 may comprise a switch or other detector, such as an optical or electronic detector, configured to detect presence of an object, provided to detect removal of the container 104 from the apparatus 100 for use. Such information can be employed by the apparatus 100 to display the time since last use of the substance.

The signals from the additional sensors 204 may be processed with or without signals from the substance and ambient temperature sensors 190 and 192, respectively. In some embodiments, combination of information from temperature, capacitive, accelerometer sensors is used to improve the sensitivity and specificity of "use" detection.

In some embodiments, the battery 200 may be disposable. Since the passive control elements do not require much power, the battery 200 may be operative for a relatively long time, such as for days, months or years. In some embodiments, the battery 200 may be rechargeable. Recharging may be performed via a recharging port or via inductance or other means which allow electrical charge generation.

In some embodiments, the apparatus 100 may comprise one or more indicators 210, such as LED indicators or a small electronic display, for example. The indicators 210 may indicate one or more environmental conditions of the substance (e.g. drug 110), such as the drug temperature, or any other parameter of the drug 110, such as color, clarity or transparency, for example. The indicators 210 may include numeric indicators, and LED's or other forms of illumination arranged in a configuration that may be intuitive to the user, such as concentric circles that indicate the time passed from last use of the apparatus 100 or container 104. For example one circle may represent the hours from the last use while the second circle provides the minutes from the use. The circles are lit in a pattern resembling the display of an analog watch. The display may also be in a form of combination of patterns and numeric digits to enable providing the user information upon passage of more than 12 hours from last use.

The indicator 210 may be configured to indicate use of the substance, the quantity of the used substance, the time the substance was last used, the last time the container 104 was opened and/or past occurrences of use of the substance. The indicator 210 may be configured to indicate that the substance was used during a passed predetermined time period, e.g. the indicator may illuminate upon a passage of two hours without use of the drug 110 as an alert that the drug 110 should be delivered.

The indicator 210 may be configured to indicate the history of the substance, such as to indicate past deviations from the required temperature range. The indicator 210 may also be configured to indicate other parameters related to the container 104 or the apparatus 100, such as the remaining battery power.

According to some embodiments, there may be provided a control capacity indicator 212 configured to display the remaining control capacity provided by the environmental control element 140 to maintain the required environmental conditions. For example, in FIGS. 1-6B, the control element 140 comprises the PCM layer 180. The PCM layer 180 is capable of absorbing the heat flux from the ambient environment until the volume of the PCM layer 180 fully liquidizes from a solid phase to a liquid phase. The PCM volume yet to undergo a phase change from solid to liquid is indicative of the remaining thermal control capacity of the control element 140.

In some embodiments, the remaining thermal capacity may be displayed to the user in any suitable indication, such as the time duration remaining until the PCM layer 180 will fully changes its phase, referred to as "$t_{remain}$". In other words, "$t_{remain}$" may be indicative of the time that remains until the PCM volume will change its phase from solid to liquid (or vice versa).

$t_{remain}$ may be calculated by any suitable method. In some embodiments, the method for calculating $t_{remain}$ may comprise: (i) Initially determining for a selected volume of a selected PCM, the total amount of time, referred to as "$t_{total}$", it takes for raising the PCM temperature to a selected temperature, referred to as $\Delta T$, while the ambient environment temperate is raised by a predetermined temperature, referred to as $\Delta Ta$. These determinations may be performed for various changes in the ambient temperature $\Delta Ta1$, $\Delta Ta2$, $\Delta Ta3$ . . . . The resultant time durations "$t_{total}$" may be stored in a memory element, such as a memory device, a memory chip, e.g. an erasable programmable read-only memory (EPROM). (ii) Thereafter, during operation of the apparatus 100, the ambient sensor 192 may detect the change in the ambient temperature since a previous detection, thereby determining $\Delta Ta$. Accordingly, the $t_{total}$ corresponding to the measured $\Delta Ta$ is retrieved from the memory device. (iii) The time passed since the commencement of the operation of the control apparatus 140, referred to as "$t_{passed}$", may be detected in any suitable manner, such as by a timer. (iv) the $t_{remain}$ may be calculated by subtracting the time passed, $t_{passed}$, from the total amount of time, $t_{total}$, it takes for raising the PCM temperature to a selected temperature by $\Delta T$, such that:

$$t_{remain} = t_{total} - t_{passed}.$$

The remaining time duration, $t_{remain}$, may be presented by indicator 212 in any suitable form, such as by an audial indication or visual display. In some embodiments, the numeral value of $t_{remain}$ may be displayed. In some embodiments, the fraction of the time remaining, $t_{remain}$, from the total time $t_{total}$ may be displayed in any suitable manner. Some exemplary displays may include: a numeral value corresponding to $t_{remain}$, $t_{total}$ or by a dial, similar to a fuel gauge on a car dashboard, or an image similar to a battery power display on a mobile phone, such as shown in FIG. 1.

A numeric non-limiting example of the above method for calculating $t_{remain}$ includes: (i) initially determining for 50 grams of a PCM with a phase change temperature threshold of 24° C., the $t_{total}$ it takes for raising the PCM temperature by 3 C.°, namely $\Delta T=3°$ C. at an ambient temperature rise of $\Delta Ta=20°$ C. It was found the total amount of time "$t_{total}$" is about 48 hours until the PCM is fully liquidized. (ii) From detecting the change in the ambient temperature since a previous detection, it was found that $\Delta Ta=20°$ C. Thus the relevant "$t_{total}$" matches "$t_{total}$"=48 hours. (iii) The "$t_{passed}$" detected by the timer was found to be 10 hours. (iv) the remaining time $t_{remain}=48-10=38$ hours of thermal control capacity.

In some embodiments, the control capacity indication may be calculated based on any one or more of the following data: the substance and ambient temperatures, embedded data relating to the apparatus 100, container 104 and thermal insulation 170, or embedded calibration data (such as container 104 related data provided by the manufacturer). Furthermore this data may be used to maintain the substance within the required environmental control range such as the temperature range, and display apparatus 100, container 104 or substance data information to the user.

In some embodiments, the PCM volume yet to undergo a phase change may be determined by a sensor 216 for detecting the phase state of the PCM layer 180. The sensor 216 may be configured to detect any changes in the phase of the PCM, such as changes in the density, volume or optical clarity of the PCM layer 108 and/or its vicinity. For example, the sensor 216 may comprise an optical sensor configured to detect changes in the PCM clarity and/or the vicinity of the PCM layer 180, either by transmission or reflection of light, indicative of changes in the volume and/or density of the PCM. In another embodiment, sensor 216 may comprise a pressure sensor configured to detect volume or density changes in the PCM and/or the vicinity of the PCM layer 180. For example, a pressure sensor may be placed intermediate the PCM layer 180 and the injection pen 108 on a wall 218 formed therebetween. Changes in the PCM phase causes changes in the volume of the PCM layer 180 applying pressure on the wall 218. This pressure is sensed by the pressure sensor.

Based on the detected changes of the PCM phase state, the remaining control capability may be determined and displayed in any suitable manner by indicator 212.

In some embodiments, an alert may be provided to indicate that the remaining control capability (e.g. $t_{remain}/t_{total}$) is significantly reduced.

In some embodiments, the apparatus 100 may comprise thermally conductive elements 219 provided for improving the uniform temperature distribution over the volume of the PCM layer 180 and/or that of the substance. The thermally conductive elements 219 may comprise may suitable configuration such as a cylindrical layer or strips, for example. The thermally conductive element 219 may be positioned in any suitable location such as intermediate the PCM layer 180 and the container 104.

The PCM type may be characterized by its phase change temperature, namely the temperature wherein the first phase fully changes to the second change, such as the temperature at which the solids completely change into liquid. In some embodiments, the PCM type may be selected, inter alia, in accordance with any one of the following parameters: the required substance temperature; the time period required for maintaining the substance at the required substance temperature (or lower or higher than a predetermined temperature threshold) and the required mode (i.e. storage or use mode of the substance, which will be described hereinbelow).

In some embodiments, several thermal insulation layers 170 having the same or different insulating parameters, and/or several PCM layers 180 of the same or different phase change temperatures may be used to achieve specific characteristics for controlling and/or maintaining the environmental conditions of the substance. Further examples of several PCM layers or PCM portions are described in reference to FIGS. 7&8.

In some embodiments, a switch 220 may be provided to activate any one of the electrical components of the apparatus 100 upon detection of insertion of the container 104 into the apparatus 100. Detection of insertion of the container 104 into the apparatus 100 may be performed in any suitable manner, such as by a pressure sensor for detecting pressure applied on the apparatus 100, for example.

Furthermore, to conserve energy of the power source, some of the indicators 210 or 212 may be configured to be inoperative at certain times. Upon detection of a predetermined event, such as insertion of the container 104 into the apparatus 100 or any other event, the indictors 210 or 212 may be activated for a predetermined time period and shut off thereafter. In some embodiments, an accelerometer, a vibration, capacitive or movement sensor may be used to detect the predetermined event.

Figure 3A:
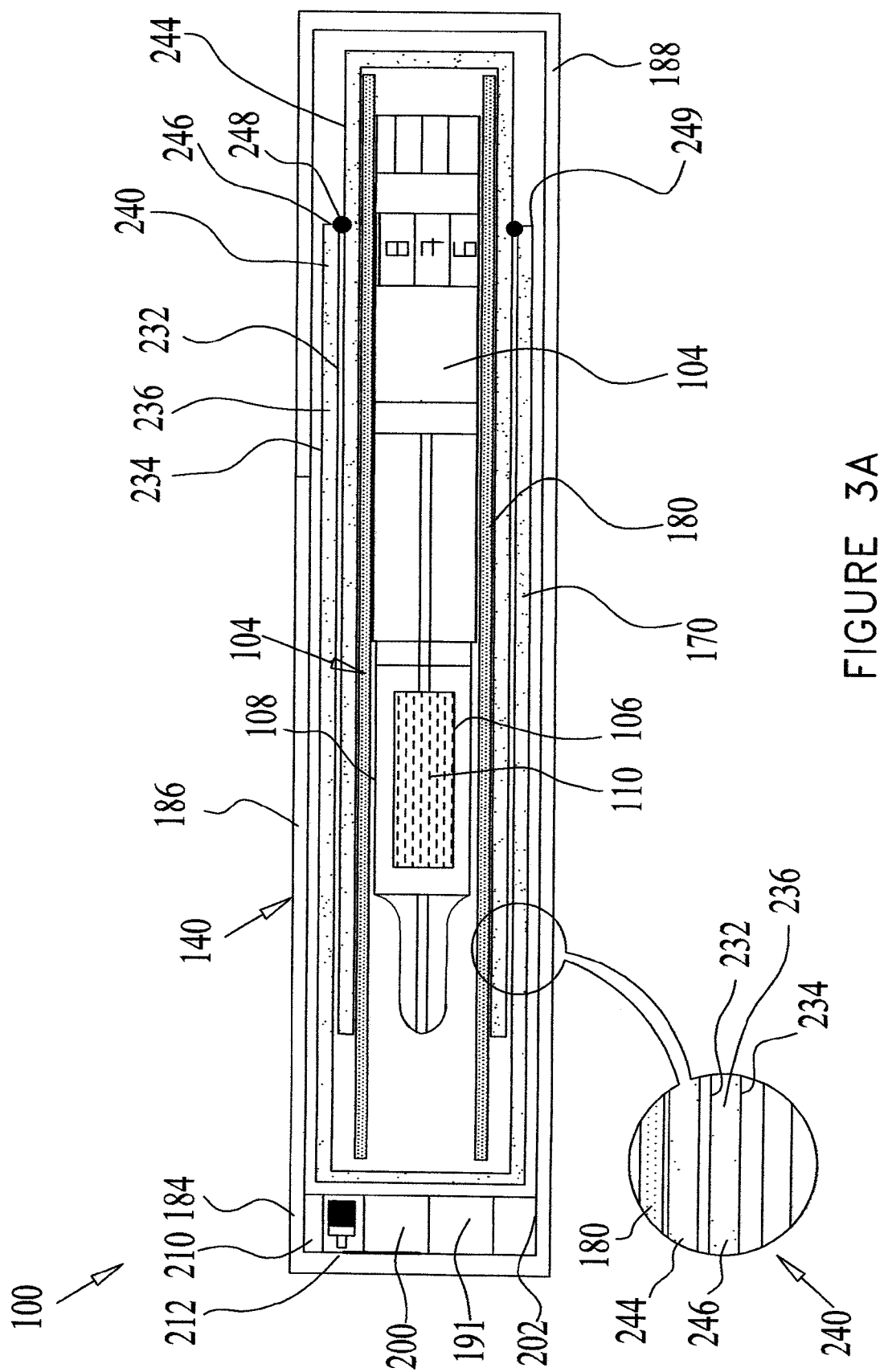
FIGS. 3A and 3B are each a schematic illustration of an exemplary environmental condition control apparatus constructed and operative according to some embodiments of the present disclosure.
Figure 3B:
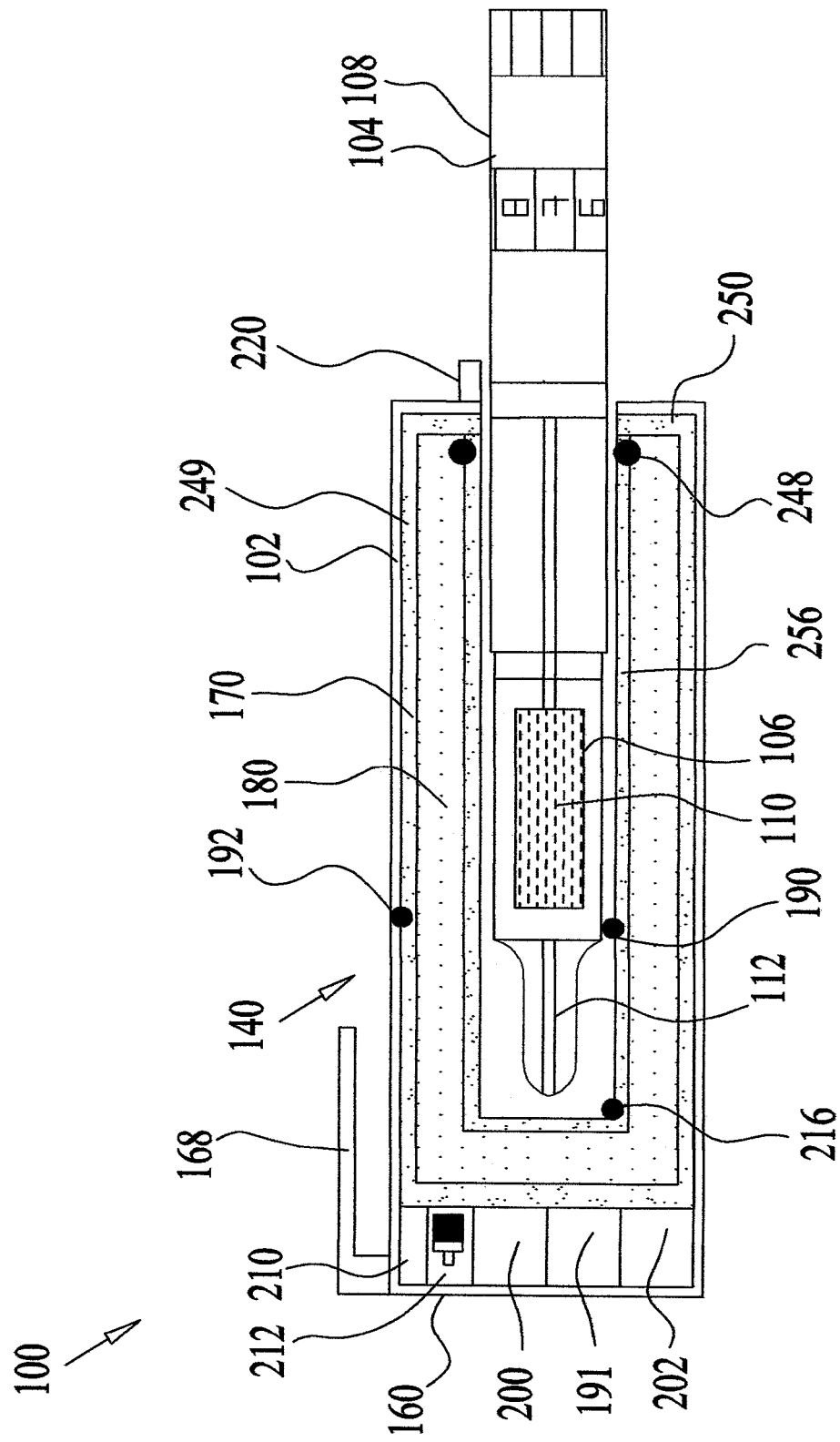
Figure 4:
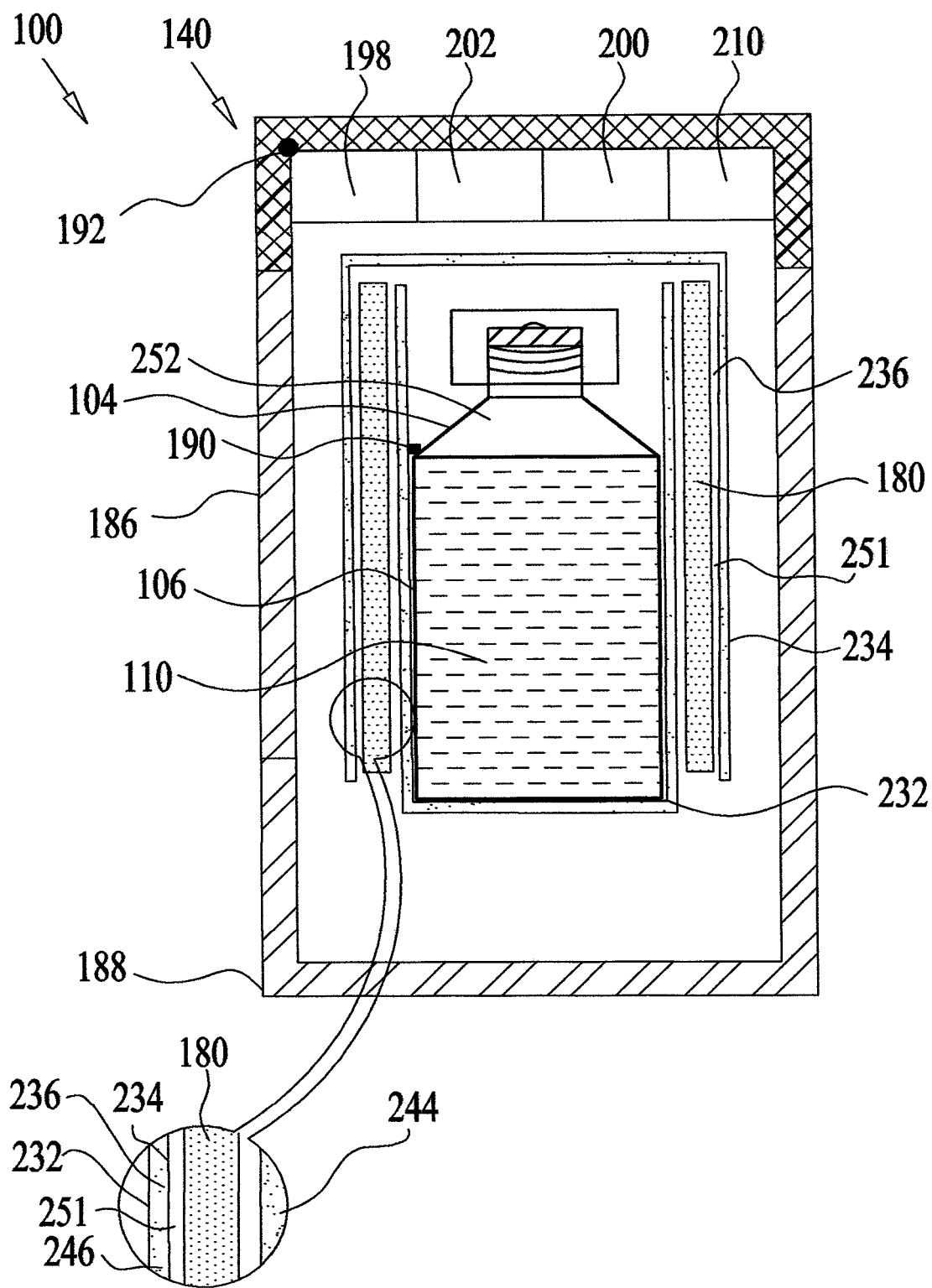
FIG. 4 is a schematic illustration of an exemplary environmental condition control apparatus constructed and operative according to some embodiments of the present disclosure.

FIGS. 3A, 3B and 4 are each a schematic illustration of the apparatus 100. As seen in FIGS. 3A, 3B and 4, in some embodiments, the thermal insulation 170 may be realized by a multi-layered material, formed of walls 232 and 234. A gap 236 defined by a space between the walls 232 and 234 may be, at least partially, evacuated. In a non-limiting example, such a thermal insulation configuration including the multi-layered material formed of walls 232 and 234 and evacuated gap 236, may be commercially available as INSULON®, made by Concept Group, Inc. (www.conceptgroupinc.com), as well as similar constructions disclosed in U.S. Publication No. 20140090737, incorporated herein by reference in its entirety. The walls 232 and 234 may be formed of stainless steel, such as stainless steel 340. Walls 232 and 234 may be vacuum brazed at both edges with the gap 236 in between the layers. In some embodiments, this gap 236 may be formed with a width of about 0.6 mm, however the gap 236 may be smaller or larger. In some embodiments, the gap width may range from about 0.3-5 mm. In some embodiments, the gap width may range from about 0.6-3 mm.

It is appreciated that the thermal insulation 170 may comprise any suitable form and may comprise any suitable material or configuration with a relatively high-vacuum structure. In a non-limiting example the high-vacuum may be about or may be about $10^{-3}$ torr or less, or about $10^{-4}$ torr or less, or may be about 10 torr or less, or may be about $10^{-6}$ torr or less, or may be about $10^{-7}$ torr or less.

In some embodiments, the vacuum within the gap 236 may be relatively high, such as about $10^{-7}$ torr, in a non-limiting example.

As seen in FIGS. 3A and 4, the thermal insulation 170 may comprise an insulating construction 240 formed of at least two mutually insertable inner and outer insulating enclosures 244 and 246. The inner insulating enclosure 244 may be formed in a cup-like shape and inserted into the oppositely facing outer insulating enclosure 246, formed in a cup-like shape as well. Insulating enclosures 244 and 246 may each comprise a multi-layered material, formed of the walls 232 and 234 wherein vacuum is established between the gap 236 formed therebetween. A sealing element 248, such as a gasket or an O-Ring, may be placed between the insulating enclosures 244 and 246 to insure an inner space enveloped between the two insulating structures 244 and 246 is sealed from the ambient environment.

In the absence of the outer insulating enclosure 246, in some but not all embodiments, heat may infiltrate into the environmental control apparatus 140 around an edge 249 of the inner insulating enclosure 244 and reach the container 104. The configuration of the two mutually insertable, oppositely facing inner and outer insulating enclosures 244 and 246, may prevent this infiltration of heat.

In some embodiments, the inner insulating enclosure 244 may be placed outwardly and the outer insulating enclosure 246 may be placed within the inner insulating enclosure 244.

In some embodiments, to allow removal of the container 104 from the tube 184 shown in FIG. 3A, the outer insulating enclosure 246 may be engaged (e.g. fixed) to the first portion 186 and the inner insulating enclosure 244 may be engaged (e.g. fixed) to the second portion 188 (or vice versa). Upon dislocating the second portion 188 from first portion 186, the inner insulating enclosure 244 is removed from the outer insulating enclosure 246 allowing the container 104 to be removed. Upon reconnecting the second portion 188 to first portion 186, the inner insulating enclosure 244 is reinserted into the outer insulating enclosure 246 to form the tightly sealed thermal insulation 170.

In some embodiments, such as shown in FIG. 3B, the thermal insulation 170 may comprise a single insulating enclosure 249 (similar to insulating enclosure 244 or insulating enclosure 244 of FIGS. 3A and 4), such as in a cap 160 configuration. The insulating enclosure 249, formed with the multi-layered material, comprising the walls 232 and 234 and evacuated gap 236 therebetween, may be formed with rims 250 and/or the sealing element 248 to form the tightly sealed thermal insulation 170.

In some embodiments, the PCM layer 180 may be arranged intermediate the insulating construction 240 and the container 104, as seen in FIG. 3A. In some embodiments, as seen in FIG. 4, the PCM layer 180, may be arranged within a space 251 formed intermediate oppositely facing inner and outer insulating enclosures 244 and 246. In some embodiments, the PCM layer 180 may be arranged intermediate the insulating construction 240 and the enclosure 102.

In FIGS. 3A and 3B the container 104 comprises the injection pen 108. In FIG. 4, the container 104 comprises a vial 252.

In some embodiments, such as in FIG. 5, the apparatus 100 may comprise an active control element in place of the passive control elements or in addition thereto, such as in addition to thermal insulation layer 170 and/or PCM layer 180.

The active control element may be configured in any suitable manner for controlling the environmental conditions of the substance. In some embodiments, the active control element may comprise means for heating and/or cooling, such as a thermoelectric element (e.g. a thermoelectric Peltier element) or a heating element 254. The heating element 254 may be configured in any suitable manner for heating the substance chamber 106, such as wherein the substance temperature deviates from a predetermined temperature (such as a maximal and/or minimal drug efficacy temperature limit). In some embodiments, the heating element 254 may comprise a warming coil. In some embodiments, the heating element 254 may comprise a rigid resistor placed within the apparatus 100. In some embodiments, the heating element 254 may comprise a flexible resistor. In some embodiments, the heating element 254 may comprise a heating laser diode. In some embodiments, the heating element 254 may comprise a heater heated by an electrical current. In some embodiments, the heating element 254 may comprise a light source for emitting thermal radiation to be absorbed by the substance chamber 106. A reflector or any other optical component may be provided to concentrate light emitted from the light source.

In some embodiments, the heating element 254 may be positioned at any suitable location, such as intermediate an inner thermal insulation layer 256 and the chamber 106. The inner thermal insulation layer 256 may be placed intermediate the PCM layer 180 and the heating element 254 to prevent inadvertent penetration of heat from the heating element 254 to the PCM layer 108.

Figure 6A:
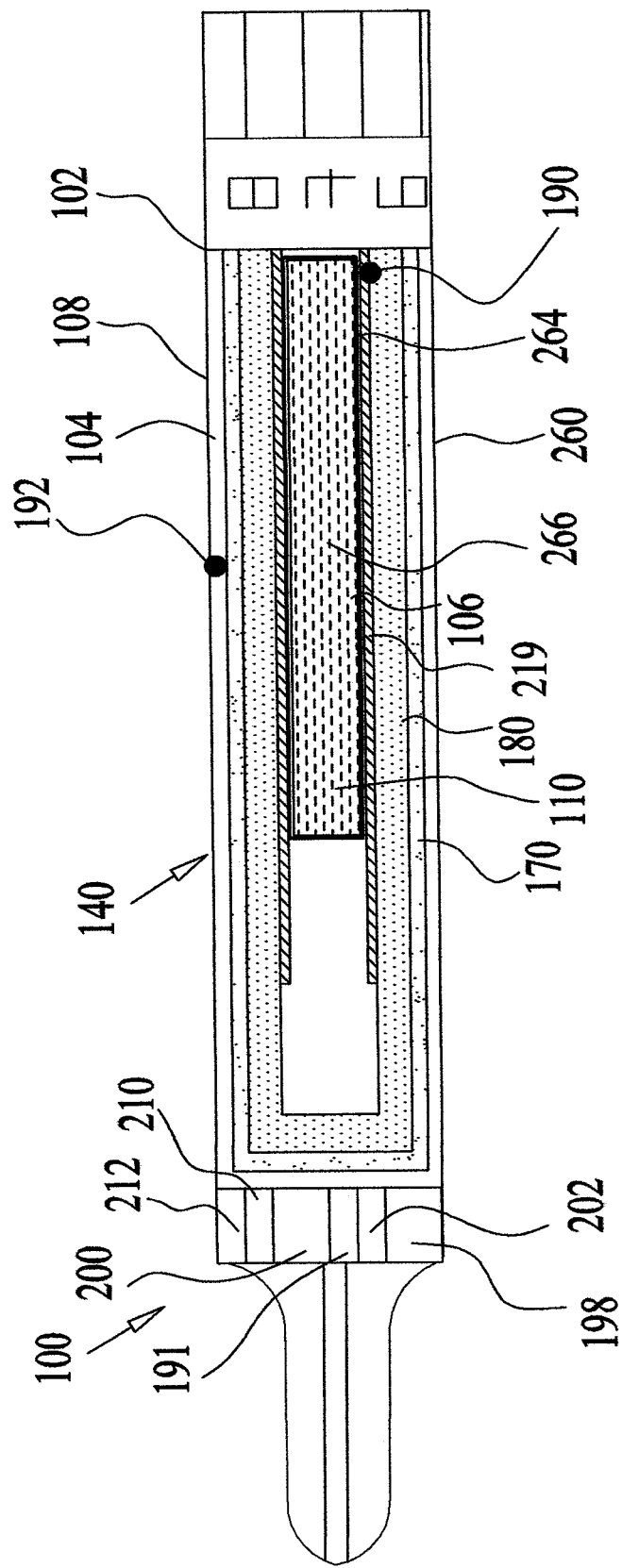
FIGS. 6A and 6B are each a schematic illustration of an exemplary environmental condition control apparatus constructed and operative according to some embodiments of the present disclosure.
Figure 6B:
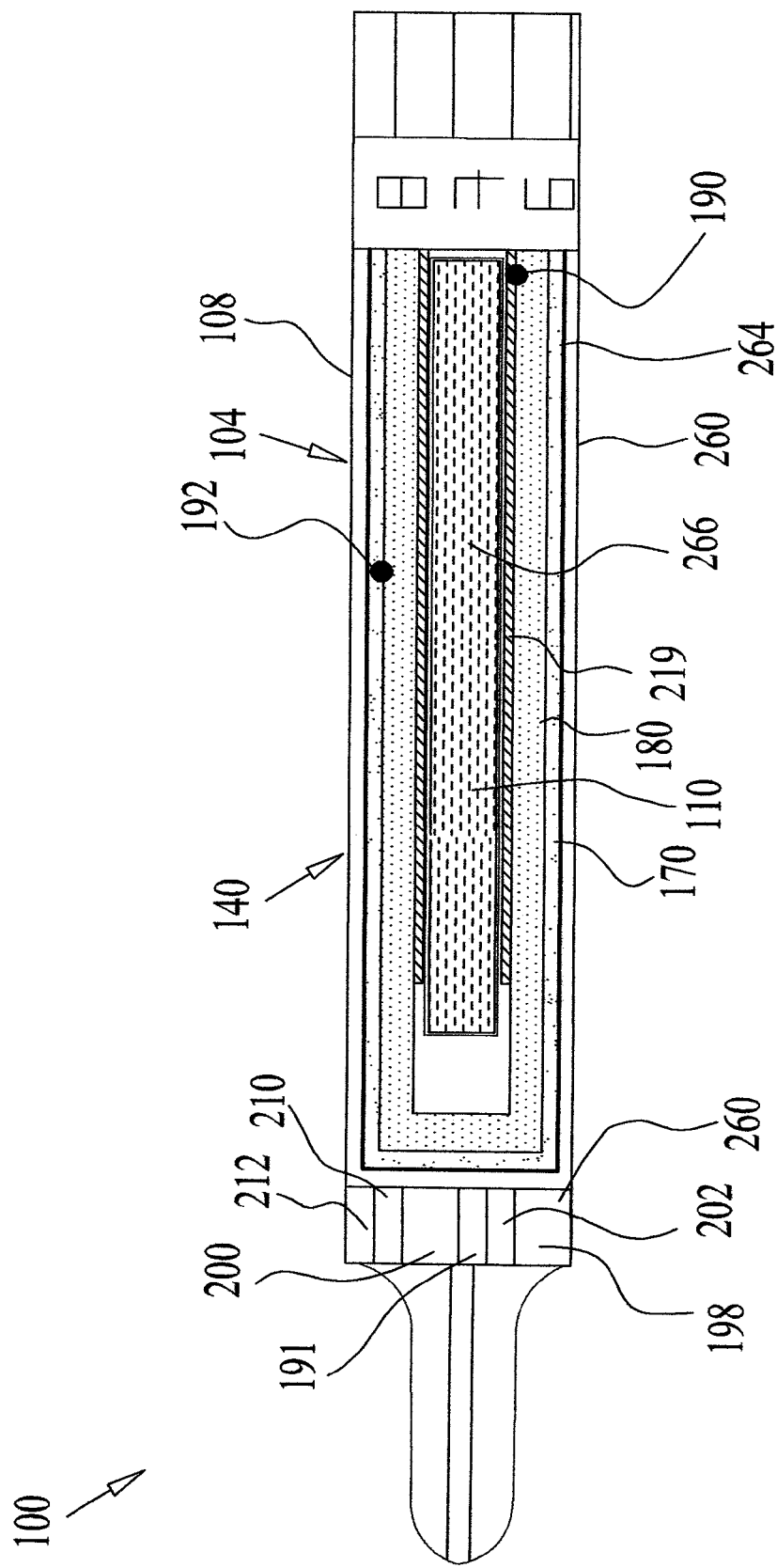

In some embodiments, such as shown in FIGS. 6A and 6B, the apparatus 100 may be integrated with the container 104 in a single enclosure 102 forming a monolithic apparatus 100 which contains the substance and comprises the environment control element 140. In some embodiments, as shown in FIG. 6A, the container 104, here shown as injection pen 108, comprises a reusable portion 260 and a disposable portion 264. The disposable portion 264 may comprise a disposable cartridge 266 comprising the substance chamber 106 containing the substance therein. The reusable portion 260 comprises the environmental control element 140, which may include any of the configurations described in reference to FIGS. 1-5, such as the thermal insulation layer 170 and the PCM layer 180. In some embodiments, the thermally conductive element 219 may be provided intermediate the PCM layer and the substance chamber 106 and in some embodiments the thermally conductive element 219 may be obviated.

The reusable portion 260 may further comprise substance temperature sensors 190 and/or ambient temperature sensors 192. The communication means 198, the battery 200, controller 191 and electronics 202, indicators 210 and control capacity indicators 212 may be embedded in the reusable portion 260 as well. Electrical communication means are provided for electrical communication between the disposable portion 264 and the reusable portion 260.

In some embodiments, as shown in FIG. 6B, the disposable portion 264 may comprise the disposable cartridge 266 with the substance chamber 106 containing the substance therein, as well as the environmental control element 140 or portions thereof. For example, the disposable portion 264 may comprise any of the configurations described in reference to FIGS. 1-5, such as the thermal insulation layer 170 overlying the PCM layer 180. The thermally conductive element 219 may be provided intermediate the PCM layer and the substance chamber 106.

In FIG. 6B the disposable portion 264 further comprises the substance temperature sensors 190 and/or ambient temperature sensors 192. The reusable portion 260 comprises the communication means 198, the battery 200, controller 191 and electronics 202, indicators 210 and control indicators 212. Yet it is appreciated that any of these components may be embedded in the disposable portion 264. Electrical communication means are provided for electrical communication between the disposable portion 264 and the reusable portion 260.

In some embodiments, different types of apparatuses 100, such as any one of the apparatuses of FIGS. 1-13B may be used during different modes. For example, the container 104 may be stored in a tube 184 (FIGS. 2A and 2B) during a substance storage mode wherein the tube 184 may be placed within a controlled environment, such as in refrigeration, for example. The PCM of the storage mode tube 184 may be selected in accordance with the controlled environment temperature. In a non-limiting example, the storage mode PCM may have a relatively low phase change temperature, such as in the range of 1-6 C.°. In some embodiments, the storage mode tube 184 may be configured for relatively long term storage, such as for days. In some embodiments, the storage term may be set to synchronize with the average use time of the container 104 so while one container 104 is in use a replacement container 104 is stored.

Prior to use of the substance, the container 104 may be transferred to an apparatus 100 used during the operation mode, such as cap 160 (FIG. 1). The PCM of the operation mode cap 160 may be selected in accordance with the ambient environment temperature. In a non-limiting example, the storage mode PCM may have a high phase change temperature, such as a phase change temperature in the range of 20-30 C.°.

In some embodiments, a single apparatus 100 may be configured for use in both storage and operation modes. The control apparatus 140 may comprise different PCMs, each configured to control the temperature at different modes, such as described in reference FIGS. 7 and 8.

Figure 8:
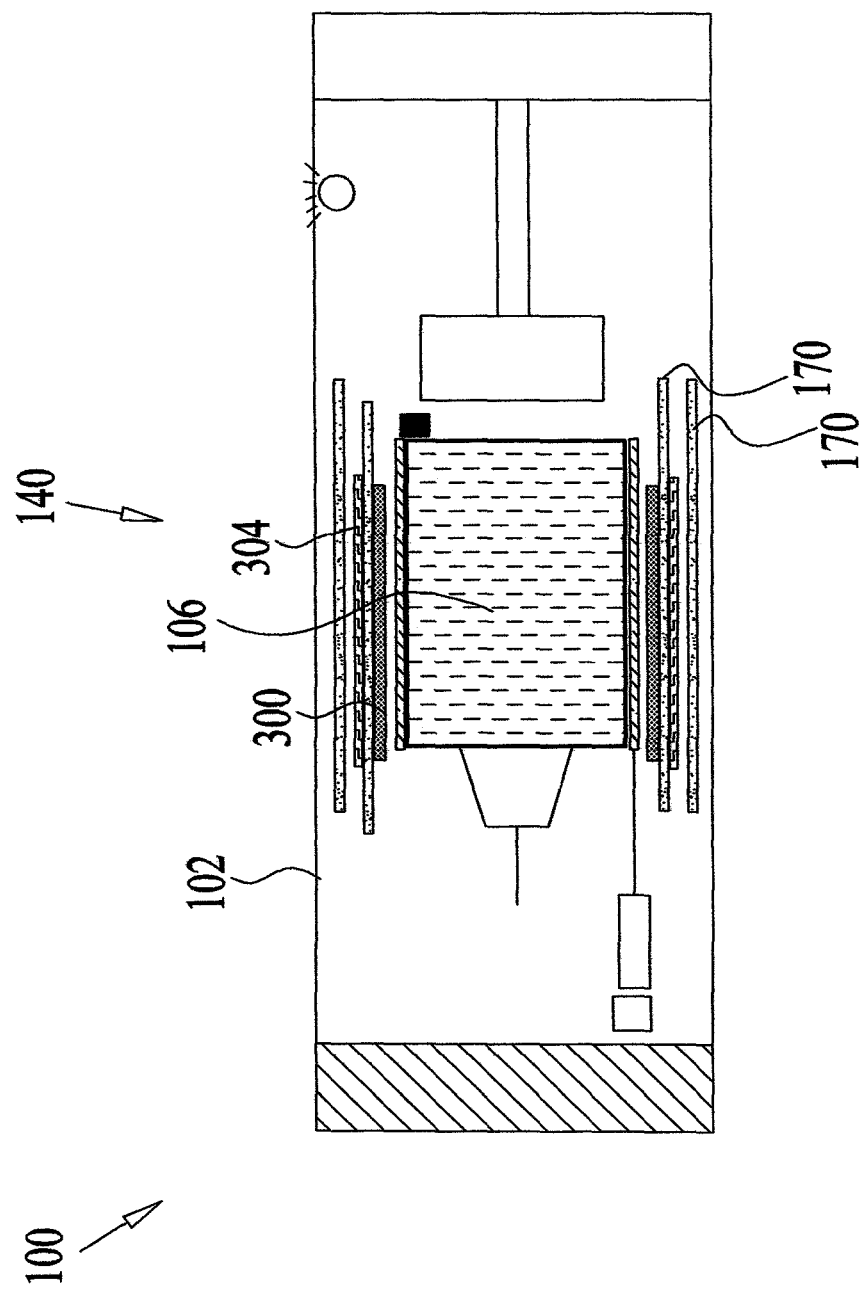
FIG. 8 is a schematic illustration of an exemplary environmental condition control apparatus constructed and operative according to some embodiments of the present disclosure.

Referring to FIGS. 7 and 8, in some embodiment, the apparatus 100 may comprise a plurality of PCM portions, where some portions 300 are configured with a relatively high phase change temperature, such as a phase change temperature in the range of 20-30 C.° and some portions 304 with a relatively low phase change temperature, such as a phase change temperature in the range of 2-6 C.°. In a non-limiting example, the high temperature PCM portions 300 may provide insulation of the container 104, such as for example, when the ambient temperature exceeds the maximal efficacy temperature of the substance. The low temperature PCM portions 304 may be used, such as for example to prevent freezing of the substance, when the ambient temperature falls below the freezing temperature of the substance or a minimal efficacy temperature of the substance.

Therefore, this combination of at least two PCM portions can control and protect the substance from both high as well as low ambient temperatures. Though two PCM portions are described, more than two different PCM can be used.

In some embodiments, the high temperature PCM portions 300 may be mixed with low temperature PCM portions 304 as shown in FIG. 7 or mixed in microencapsulation or mixed when one is microencapsulated while the other is not, or may be placed adjacent thereto.

In some embodiments, the PCM may be in bulk form or in microencapsulated form or any other suitable form. Microencapsulation allows mixing of different PCM's with different phase transition temperatures while in bulk form each type of PCM may be formed as separate layers.

In some embodiments, the PCM portions 300 and/or 304 may be formed as layers and may be arranged in proximity or adjacently thereto, as shown in FIG. 8.

The PCM portion 300 and/or 304 may be placed at any suitable location within the apparatus 100.

In some embodiments, the PCM portion 300 and/or 304 may be placed intermediate the thermal insulation 170 and the substance chamber 106, as shown in FIG. 7. In some embodiments the thermal insulation 170 may be placed intermediate the PCM portions 300 and/or 304 as shown in FIG. 8 in place or in addition to the thermal insulation placed intermediate the PCM portion 300 and/or 304 and enclosure 102.

In some embodiments, different types of apparatuses 100, such as any one of the apparatuses of FIGS. 1-12, may be employed without the user's intervention or in other words, the apparatus 100 may comprise a thermally self-recharging apparatus 100. This may be achieved by selecting a PCM according to ambient temperature fluctuations, appropriate volume and according to the substance temperature maximal or minimal limit. For example, by selecting a PCM with a phase change temperature equal or slightly below the maximal substance temperature limit and selecting a PCM volume configured to remain at a solid phase for a predetermined time period, the substance may be safely maintained below the maximal substance temperature limit for a relatively long period, including during use and/or storage of the container 104 within the apparatus 100, without any intervention. The intervention may include, for example, requiring the user to refrigerate the apparatus 100 to recharge the PCM layer from a liquid phase to a solid phase.

In a non-limiting example for such a nonintervention apparatus 100 (namely, thermally self-recharging), a substance comprising insulin or epinephrine may retain its efficacy for 28 days if maintained in a temperature below 30° C. with a sufficient volume (e.g. 3 times the volume of the chamber 106) for a predetermined time period (e.g. 18 hours). By selecting a PCM layer 180 with a phase change temperature close to the temperature limit of 30° C., such as 28° C. or 29° C., with the PCM sufficient volume, the chamber 106 will not exceed the 30° C. limit as long as the PCM layer 180 does not completely change its phase from solid to liquid. Thus even if the apparatus 100 is placed in an ambient temperature of over 30° C. for slightly less than 18 hours, the insulin or epinephrine will remain below 30° C. Whereupon the ambient environment returns to temperature below the phase transition of the PCM (e.g. below 28° C. or 29° C.), such as room temperature, the PCM layer 180 will start to solidify again, without requiring the user to perform any special action or intervention.

Referring to FIGS. 9-13, the apparatus 100 may comprise a rapid temperature change apparatus configured to rapidly change the temperature of the substance, such as a heating apparatus provided to elevate the temperature of the substance.

Many drugs and other substances have limited boundaries to such conditions that if exceeded, can degrade the drug activity or degrade the substance. Some drugs are sensitive to temperature and may be degraded by exposure to above a limited, maximal temperature. While maintaining the drug efficacy requires certain conditions, using the drugs may require, or have preference to different conditions. For example, a drug 110 may be required to be maintained refrigerated (2-8° C.) while it is preferable to be delivered at room temperature, around 25° C. Sometimes, the drug temperatures are required to rapidly change from one condition to the other, for example, from storage temperature of 2-8° C. to use temperature of around 25° C., within less than 60 seconds. This facilitates the relatively immediate drug use by the user, not requiring the user to wait long time before the drug, removed from the refrigerator, can be used.

Even for a small volume of substances (e.g 1-10 ml) it is difficult to achieve this rapid temperature change, without exposing the drug to temperatures above the limit efficacy temperature. For containers 104 that are handheld, it may also be difficult to achieve this fast temperature change without exposing the user's hand to dangerously high temperatures.

For example, in order to warm up a drug which was kept refrigerated, faster warming induces higher temperatures. However, the drug 110 might be degraded if exposed to such high temperatures, even for short time periods. Therefore, the drug heat for changing its temperature, should be limited and controlled during the entire time (or some of the time) of the exposure, in order to prevent degradation or otherwise cause any harm to the drug 110 and furthermore without causing any harm to the user's holding hand (i.e. burning due to extreme heat).

Figure 9:
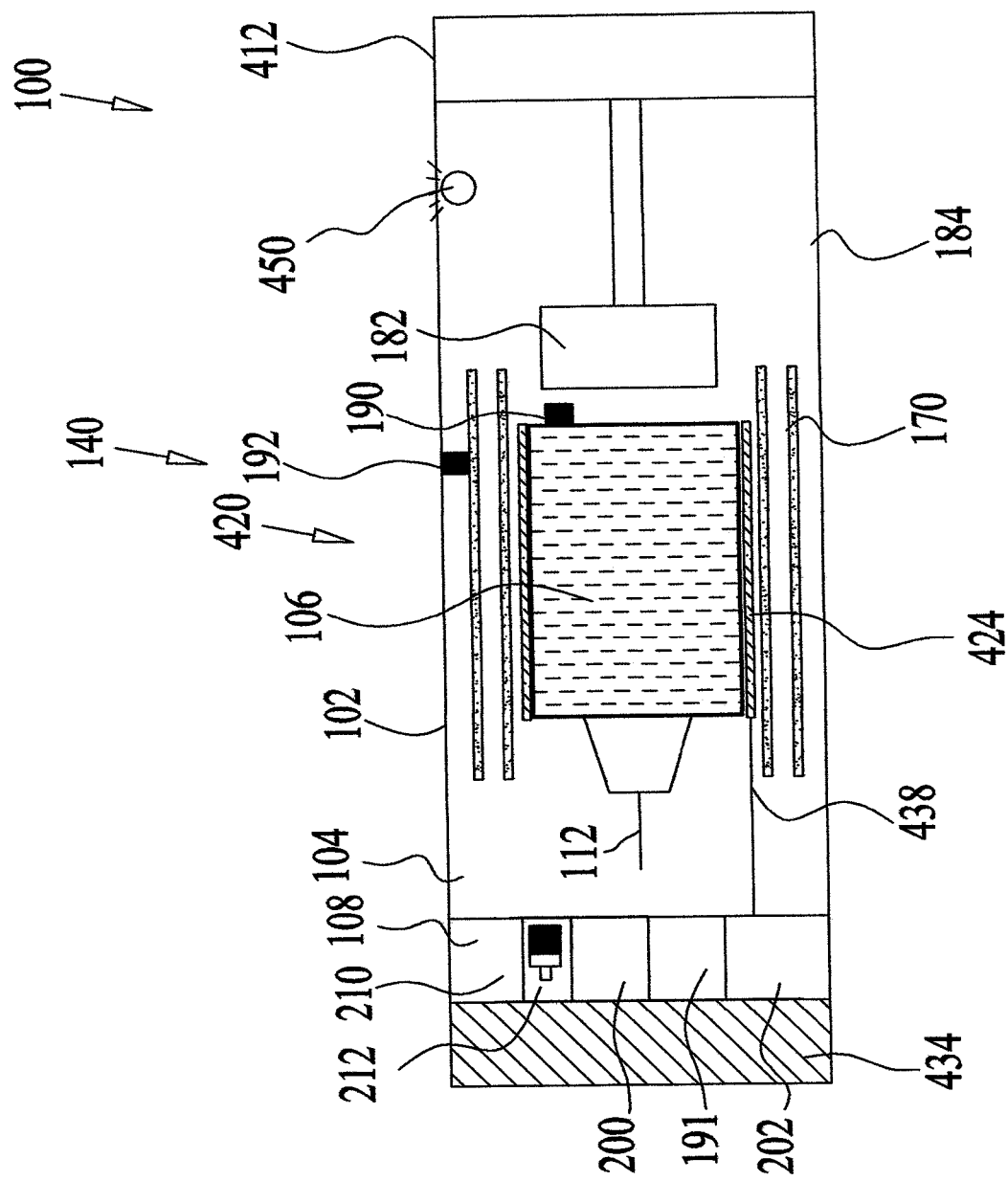
FIG. 9 is a schematic illustration of an exemplary environmental condition control apparatus constructed and operative according to some embodiments of the present disclosure.

In the embodiment of FIG. 9 the container 104 is integrated into the apparatus 100 in a single enclosure 102 forming a monolithic apparatus 100 shaped as a tube 184. The apparatus 100 may comprise a locking mechanism 412 which upon release allows a retractable needle 112 to be pushed by the plunger 182. The environmental control element 140 may include a heating assembly 420 for heating the substance chamber 106. The heating assembly 420 may comprise a heating element 424. The heating element 424 may comprise any suitable mechanism, such as an electrical mechanism, a chemical reaction, an optical mechanism, RF and a microwave mechanism, for example or the heating element 254 of FIG. 5.

The heating element 424 may be powered by a power source, such as battery 200. Thermal insulation 170 configured as a thermal directive barrier may be provided to prevent escape of the heat from the substance chamber 106 and for channeling the heat to the substance chamber 106, as well as preventing singeing a user's hand.

Upon removal of the container 104, here comprising an injection device 108, from refrigeration or any other environment where the substance chamber 106 was retained at an initial temperature, the user may activate a safety and release mechanism 434. The release mechanism 434 may be configured to be pulled away for enabling the battery 200 to contact electrical contacts 438 of an electrical circuit for activating the heating element 424 to raise the substance chamber temperature from the initial temperature to an elevated, predetermined temperature. The heating duration and temperature may be based on a signal received by the controller 191 from the substance temperature sensors 190 and/or the ambient temperature sensors 192. Thus the elevated temperature does not exceed a limiting temperature altering the properties of the drug as well as preventing singeing the user's hand. The temperature sensor 190 or 192 or any temperature sensitive element may be used to control the current flow in the electrical circuit.

In some embodiments, electrical heating by the heating element 424 may be performed by conducting a current through a resistor, which is optimized to generate heat. The temperature sensor 190 may be used to control the temperature along with the controller 191 operative to cease the heating whereupon the temperature reading reaches a limit temperature. In some embodiments, if the temperature sensor 190 is such that its electrical properties change with the temperature change, the temperature control can also be achieved without a controller 191. This may be performed by designing the electrical circuit to stop conducting current to the heating element 424 when the electrical properties of the temperature sensor 190 (like resistance), reaches a limit which corresponds to a limit temperature.

In some embodiments, the heating element 424 may heat by employing an electrical mechanism, a chemical reaction, an optical mechanism, RF or microwave, for example.

In some embodiments, the battery 200, electrical circuit and the heating element 424, are designed such that the battery 200 can provide substantially the adequate amount of power to the heating element 424 sufficient to generate the required amount of heat over time.

In some embodiments, heating is achieved by a chemical reaction generated by the heating element 424. The temperature reached by the chemical reaction may be designed to generate a substantially adequate amount of heat over time, thereby obviating the need for a temperature sensor 190 or 192.

In some embodiments, the heat is directed to surround the substance chamber 106 due to the thermal insulation 170. Upon reaching the elevated predetermined temperature or after passage of a predetermined timespan, an indicator 450 may indicate to the user that he may commence injection or use process by releasing the locking mechanism 434 and inject or otherwise use the drug or substance. The indicator 450 may be sensed by the user in any suitable manner such as by an audible, visual or vibration indication, for example.

In some embodiments, the initial temperature may be in the range of 0-7 C.° and the elevated temperature may be in the range of 20-30 C.°' for example. Heating from the initial to the elevated temperature may be achieved relatively rapidly, such as within a duration of 60 seconds or less, or anytime between 1-5 minutes, for example.

Figure 10:
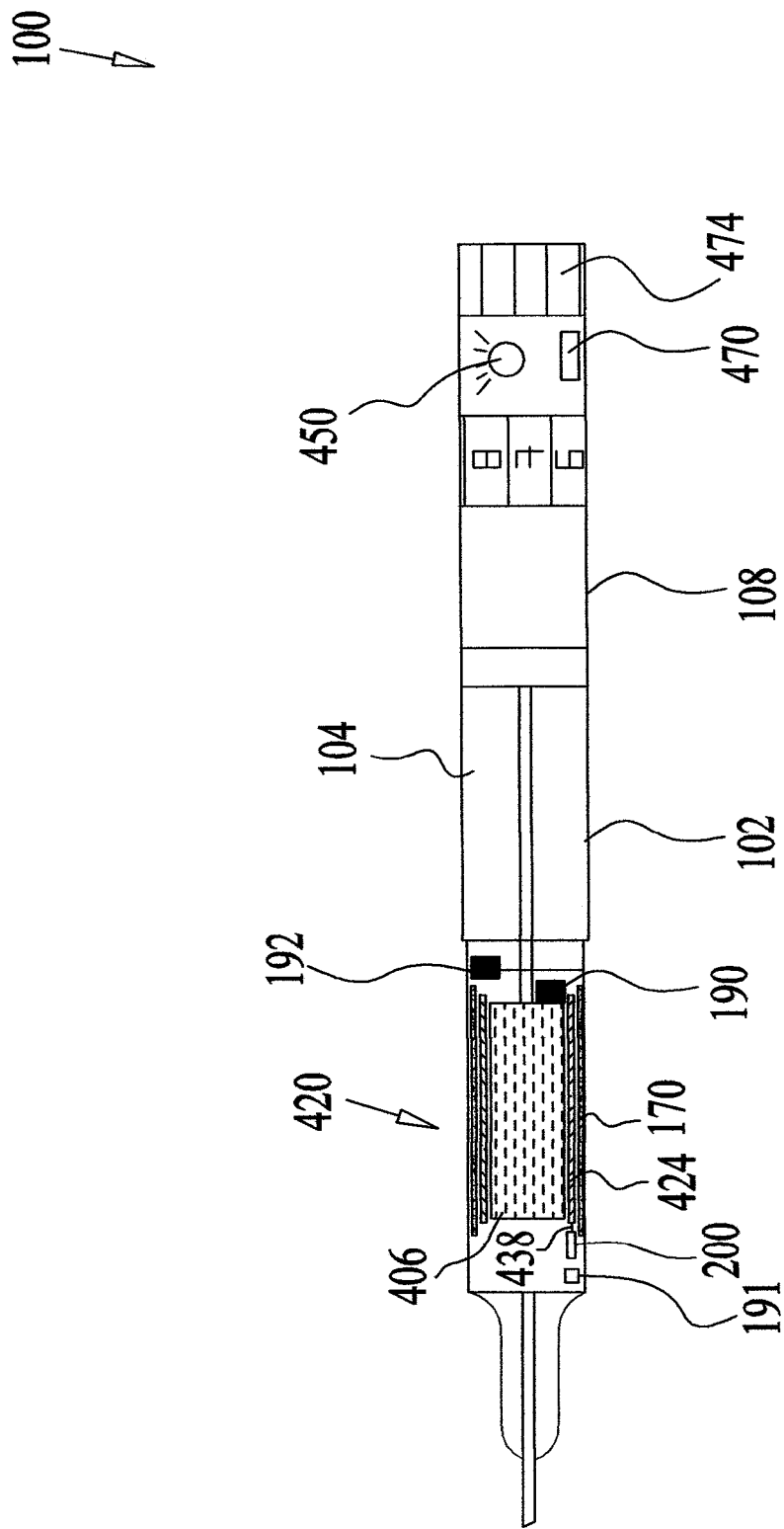
FIG. 10 is a schematic illustration of an exemplary environmental condition control apparatus constructed and operative according to some embodiments of the present disclosure.
Figure 11:
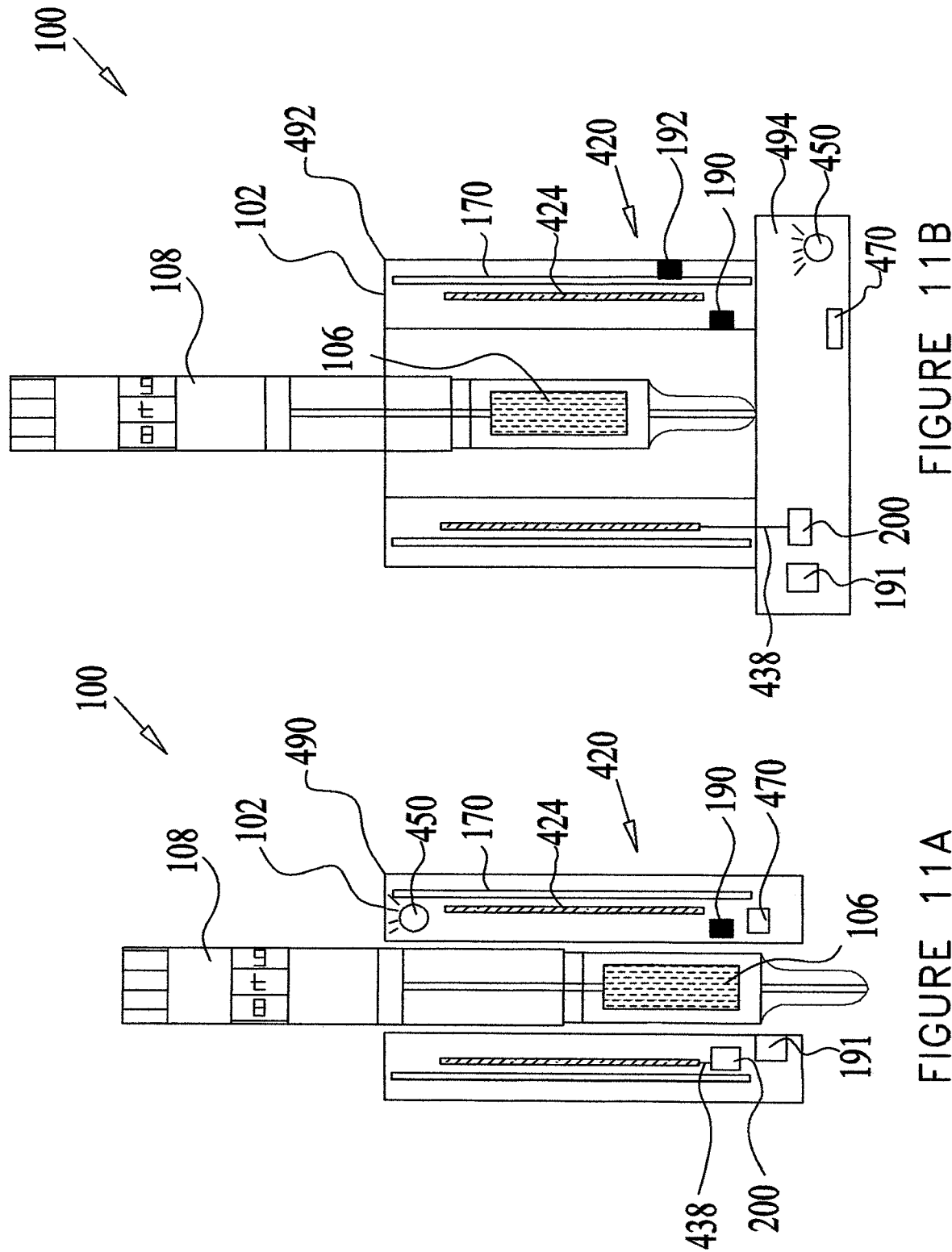
FIGS. 11A and 11B are each a schematic illustration of an exemplary environmental condition control apparatus constructed and operative according to some embodiments of the present disclosure.

Referring to FIG. 10, the container 104 is integrated into the apparatus 100 in a single enclosure 102 forming a monolithic apparatus 100 configured as an injection device, such as an injection pen 108. The injection device may be configured for multiple use and may be reusable or may be configured for a single or few uses and may be disposable.

For example, as shown in FIG. 10, the apparatus 100 may be a reusable injection pen configured for housing a replaceable drug cartridge comprising a drug, which is retained within the substance chamber 106. In some embodiments, the apparatus 100 may be a prefilled (or pre-loaded), disposable injection pen.

The apparatus 100 may comprise the heating assembly 420 formed therein for heating the substance chamber 106 by the battery 200.

Upon removal of the apparatus 100 from refrigeration or any other environment with a chamber initial temperature, the heating assembly 420 may be activated in any suitable manner. In some embodiments, removal of a cap from the apparatus 100 may impel the battery 200 to contact electrical contacts 438 of an electrical circuit for activating the heating element 424 to raise the chamber temperature from the initial temperature to an elevated, predetermined temperature. In some embodiments, a switch 470 may be pressed to activate the heating element 424. The heating duration and temperature may be based on a signal received by the controller 191 from the substance temperature sensor or sensors 190 and ambient temperature sensors 192.

The heat is directed to surround the substance chamber 106 by the thermal insulation 170. Upon reaching the elevated predetermined temperature or after passage of a predetermined timespan, the indicator 450 may indicate to the user that he may commence injection generally by setting the desired substance volume and pressing a push-button 474 to inject the drug or substance.

Referring to FIGS. 11A and 11B, the apparatus 100 may be configured separately from the container 104 and formed with a volume for receiving the container 104. The container 104 may be a standard, commercial injection device, such as a syringe or injection pen 108 for example. The apparatus 100 may be formed as a sleeve 490 as shown in FIG. 11A wherein the battery 200 and electronic components are positioned within the sleeve cylindrical enclosure 102. The apparatus 100 may be formed as a tube 492 as shown in FIG. 11B wherein the battery 200 and electronic components are positioned within a tube base 494.

The apparatus 100 of FIGS. 11A and 11B may comprise the heating assembly 420 and further features described in reference to FIGS. 9 and 10.

Figure 12:
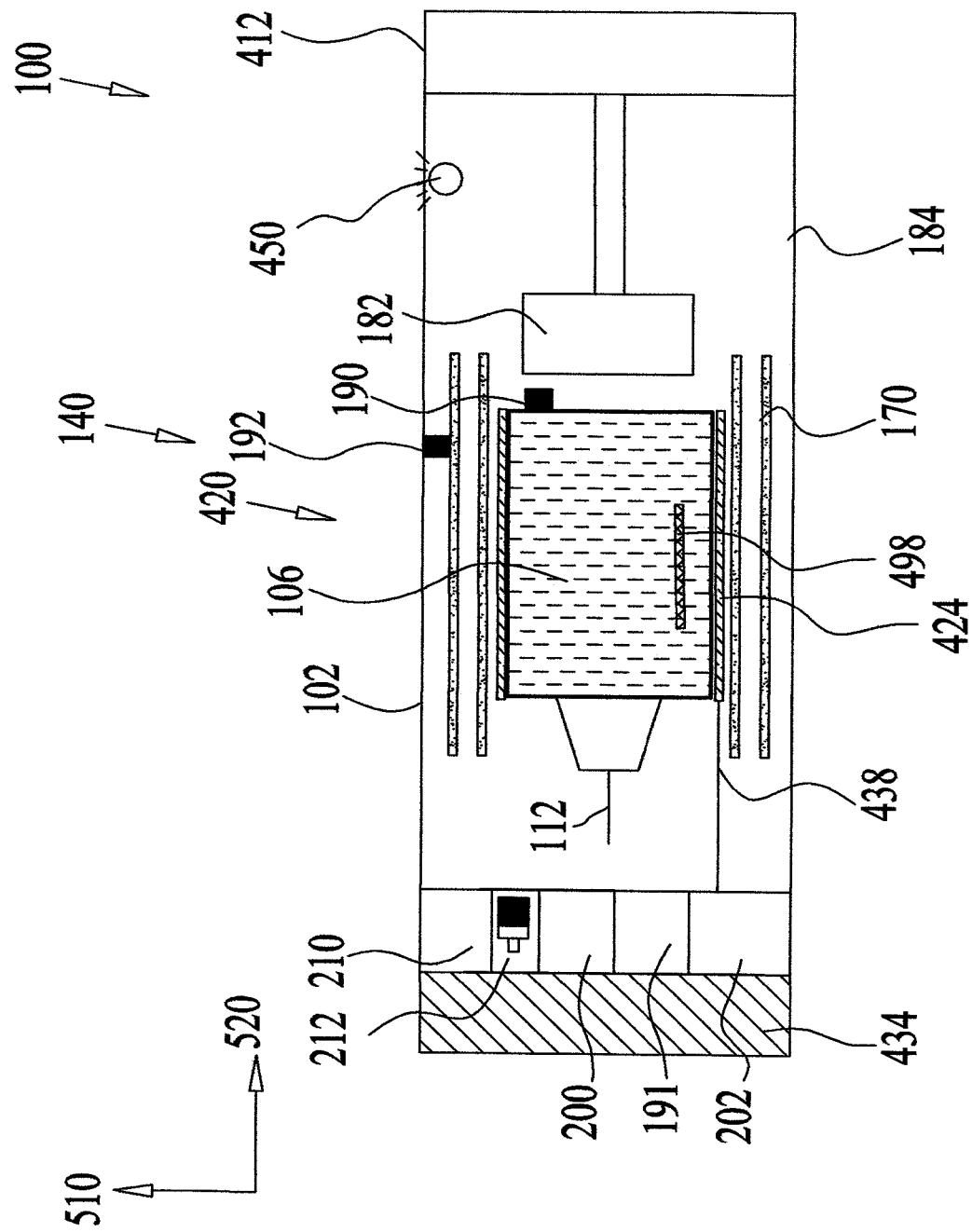
FIG. 12 is a schematic illustration of an exemplary environmental condition control apparatus constructed and operative according to some embodiments of the present disclosure.

Referring to FIG. 12, apparatus 100 may be formed similarly to apparatus 100 of FIG. 9 or any other apparatus 100, yet the heating subassembly 420 may include an internal heating element 498. The internal heating element 498 may be placed on the wall of the substance chamber 106 or may be in physical and/or thermal contact therewith. The internal heating element 498 is configured to heat the substance and may be provided in addition to heating element 424 or may replace it. As the internal heating element 498 heats the substance, the thermal insulation 170 may channel the escaped heat to the vicinity of the substance chamber 106.

The internal heating element 498 may comprise any suitable heating element configured to heat the substance from the initial temperature to the elevated, predetermined temperature. In some embodiments, the internal heating element 494 may be configured as a metal strip or any sufficient heat conductor in electrical communication with the battery 200 or as the heating element 424 or heating element 254 of FIG. 5. In some embodiments, the internal heating element 498 may be attached to the plunger 182 or walls of the substance chamber 106 or any other location for heating the substance chamber 106.

In some embodiments, the heating element 498 may be heated by induction or by any suitable manner.

In some embodiments, the thermal insulation 170 comprising the multi-layered walls 232 and 234 and evacuated gap 236 (FIGS. 3A and 3B) or any other form, may channel heat escaping the heating element 424 or 498 to dissipate in the direction of an arrow 510, perpendicularly to a longitudinal axis 520 of the apparatuses 100 of FIGS. 1-13. Accordingly the escaped heat remains in the vicinity of the substance chamber 106, In other words, the thermal insulation 170 may be configured to block the heat conduction and heat convection while minimizing radiative heat transfer to a certain direction thereby channeling the heat flow to a preferred direction.

Figure 13A:
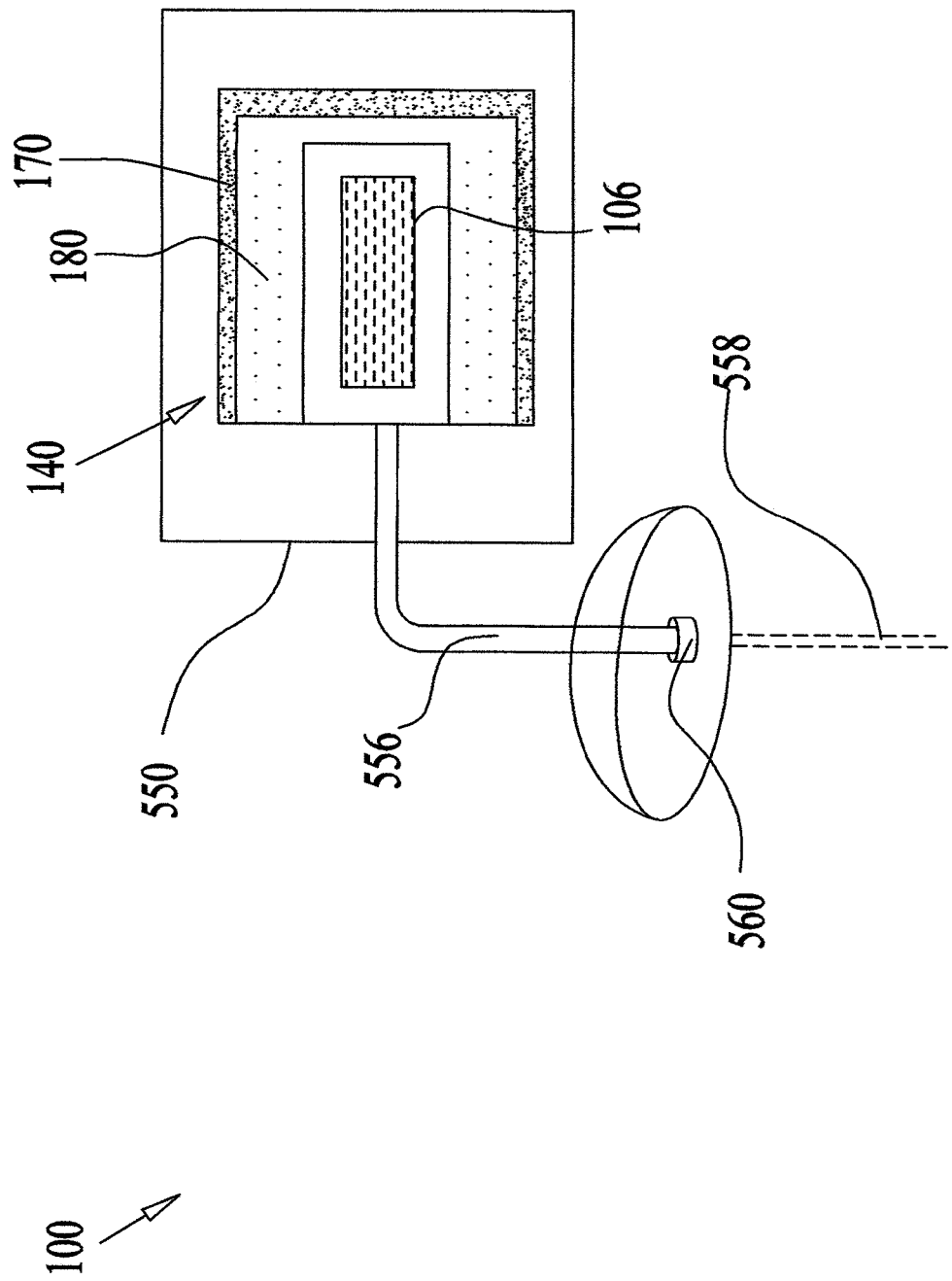
FIGS. 13A and 13B are each a schematic illustration of an exemplary environmental condition control apparatus constructed and operative according to some embodiments of the present disclosure.
Figure 13B:
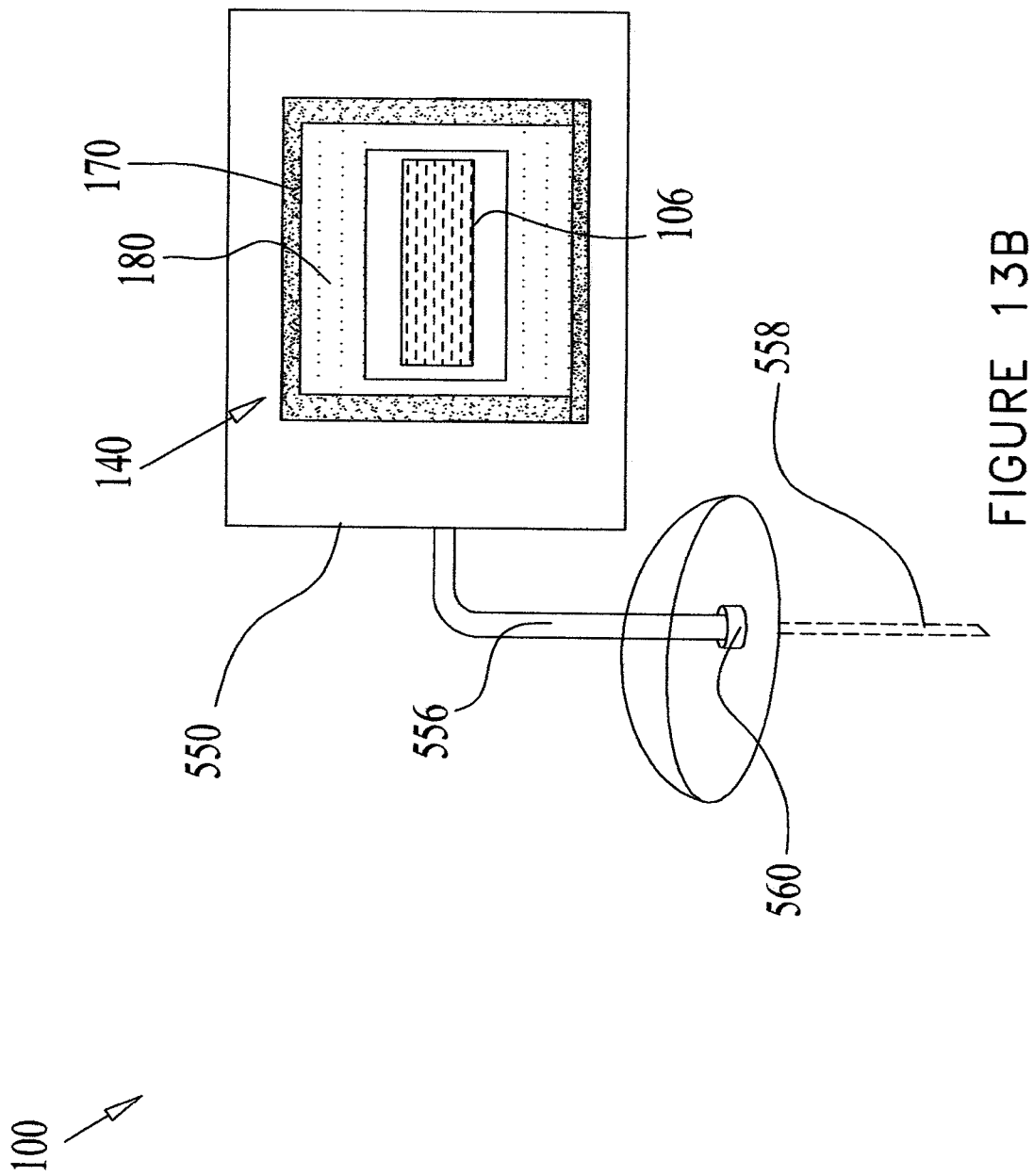

Referring to FIGS. 13A and 13B, apparatus 100 comprises the container 104 formed as a substance pump 550, for delivery of the substance by infusion. The pump 550 comprises a substance reservoir which contains the substance chamber 106, The substance chamber 106 may be integrated into the pump 550 or may be a replaceable cartridge. The pump 550 may comprise the environmental control element 140 residing within the pump 550 around the substance chamber 106. As seen in FIGS. 13A and 13B the environmental control element 140 may comprise the thermal insulation 170 and at least one PCM layer 180. FIG. 13A, the thermal insulation 170 and the PCM layer surround the substance chamber 106 or may fully surround the substance chamber 106, as seen in FIG. 13B.

The pump 550 may have more than one substance chambers 106 each with its own environmental control element 140 or all may share the same environmental control element 140. Substances in the pump 550 may be in liquid form or liquid and powder form requires mixing prior to infusion. While some substances may require environmental control elements 140 to maintain their conditions, other substances like those in powder form may not require that or may require different condition control, such as maintenance of a different maximal limit temperature than the liquid maximal limit temperature.

In some embodiments, the environmental control element 140 may comprise the thermal insulation 170 only. In some embodiments the environmental control element 140 may further comprise active elements, described herein. The environmental control element 140 may comprise any configuration described in reference to FIGS. 1-12.

The pump 550 may be a tubed pump as seen in FIGS. 13A and 13B, comprising a catheter 556 formed, on one end thereof, with a cannula 558, which can be inserted into a the user's tissue. In some embodiments, a connector 560 can connect between catheter parts or between the catheter 556 and the cannula 558. Catheter 556 can be connected to the drug chamber 106 and to the infusion pump 550, provided for control of the drug delivery from the chamber 106.

In some embodiments, providing a pump 550 with the environmental control element 140 configured to control the environmental conditions (e.g. pressure, temperature) in the substance chamber, prevents or minimizes pump occlusion which may be caused, for example, due to drug exposure to uncontrolled environmental conditions causing drug degradation and crystallization which in turn interrupts the drug path from the chamber 106 to the tissue. In some embodiments, the pump 550 may be a tubeless pump, such as a patch pump, for example. In this case the catheter 556, connecting the drug chamber 106 to the cannula 558, may reside within the pump 550 or is omitted and the cannula 558 is directly connected to the drug chamber 106 of the pump 550.

According to some embodiments of the present disclosure there is provided a method for determining the amount of substance remaining in the substance chamber 106, such as after delivery or any other use of the substance.

Figure 13C:
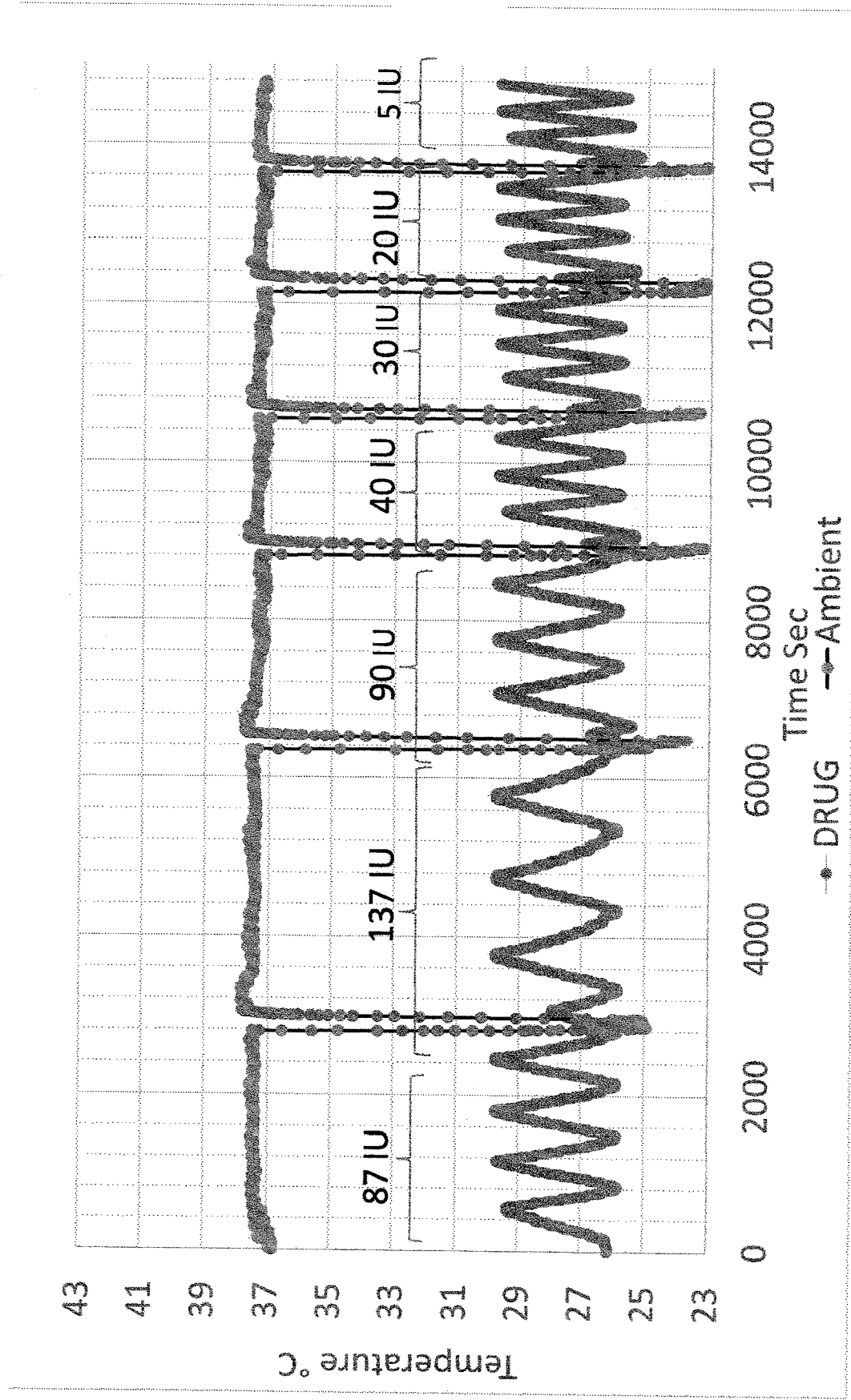
FIG. 13C is a graph showing change in temperature of a substance, placed within an environmental condition control apparatus, as a function of time.

FIG. 13C is a graph showing change in temperature of insulin as a function of time. The drug in the injection pen within a control apparatus was heated by a heating element comprising an oven to raise its temperature by 3 C.° and to cool it by 3 C.°, as shown by the lighter line. Different drug volumes were heated (e.g. a volume of 87 IU, 137 IU etc.). The ambient temperature is shown by the darker line. A drop in the ambient temperature is seen following a number of the substance heating cycles. This occurred upon removal of the injection pen from the control apparatus, when the control apparatus was removed from the oven to remove the injection pen therefrom so as to change the substance volume.

Figure 13D:
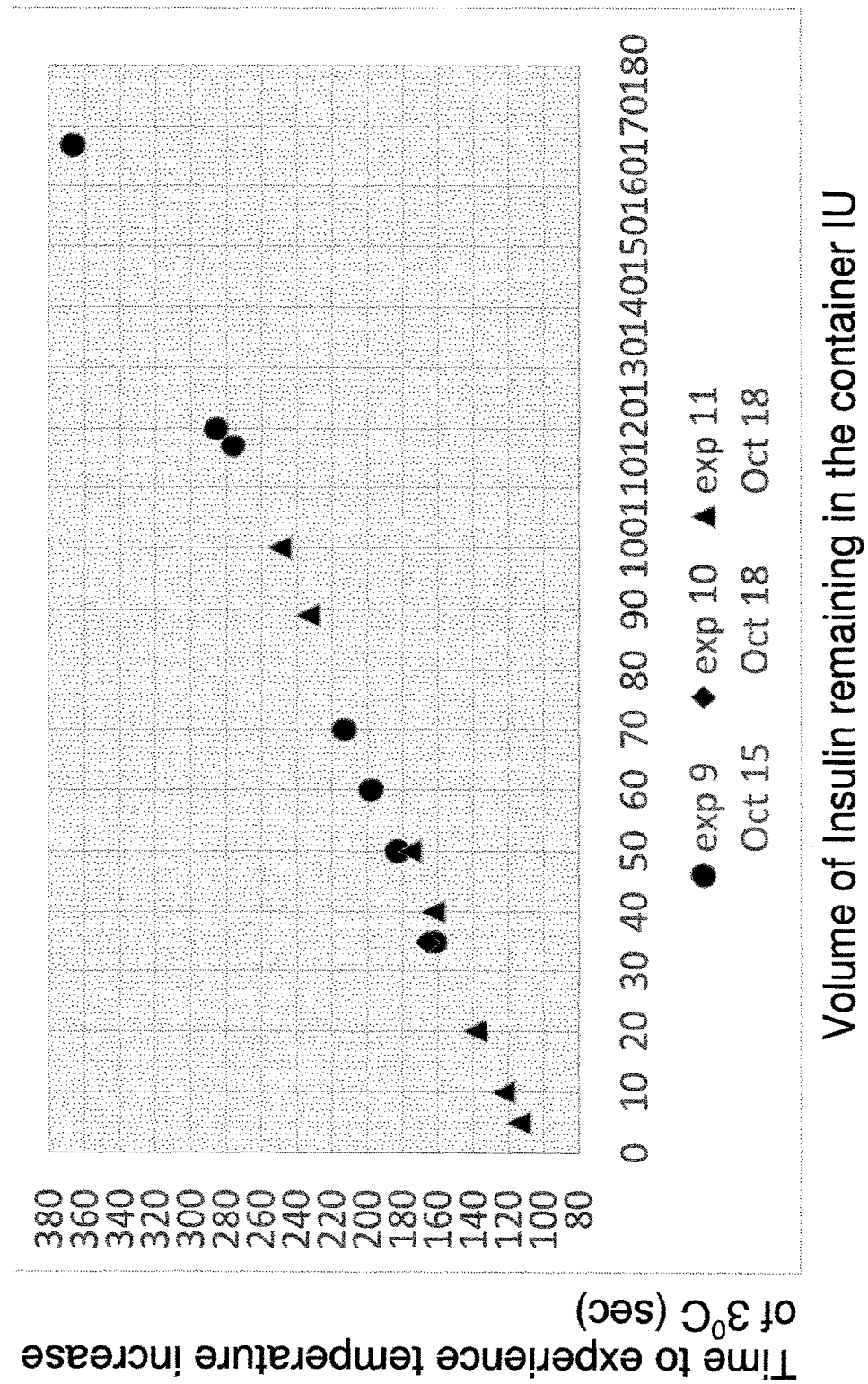
FIG. 13D is a graph showing the correlation between the time it took for the substance within an environmental condition control apparatus to undergo a specific temperature change and the volume of the substance.

FIG. 13D is a graph showing the correlation between the time duration it took for insulin within the control apparatus to undergo a 3 C.° temperature change and the volume of the remaining insulin within the injection pen. The volume change was observed on various days. It is apparent that there is a robust linear relationship between the time duration and the volume change.

As shown in FIGS. 13C and 13D, there is provided a method for determining the amount of substance remaining in the substance chamber 106 or any of the apparatus 100 described herein in FIGS. 1-13B. The method may include calculating the amount of substance remaining in the chamber 104 by at least one of the following: measuring the time for a selected volume of the substance to experience a specific temperature change, storing these measurements in the memory element, and during a selected time activating the heating element (e.g. heating element 254 of FIG. 5) to achieve the specific temperature change and comparing the time required for that to the stored times, to determine the amount of remaining substance.

According to some embodiments of the present disclosure there is provided the control element 140 for maintaining drugs contained in the containers 104 within a specific temperature range and for providing information related to the capacity of the control element 140 to maintain the specific temperature range.

The heating element 254 may comprise a heating coil arranged in the enclosure 102 to be in close proximity to the chamber 106. The heating coil may be insulated from the PCM 180, and may be used to calculate the amount of drug residing in the chamber 106, as described herein:

There are provided according to some embodiments of the present disclosure, systems and methods for calculating a quantity of the substance within the chamber 106 prior to or after delivery of the substance. The quantity may be measured in any suitable manner, such as the mass, weight, volume or units of the substance, for example.

According to one method, the quantity of the substance may be calculated by measurement of temperature changes, or other parameters related to the temperature change, within the substance over a predetermined time span. In some embodiments, the measurement of the temperature changes or the other parameters, may be performed using any one of the apparatuses 100 described in reference to FIG. 1-13B or 14-20B.

In other words, the reading from the ambient temperature sensor 192 and the reading from the substance temperature sensor 190 may be used to determine the quantity of drug in the container chamber 106 and the quantity of drug removed from the chamber 106.

For example, the quantity calculating system for calculating the substance quantity may include a clock, counter or timer configured to record the passage of time span "1" (i.e. duration) during a predetermined temperature change "$\Delta T$" (e.g. heating and/or cooling) of the substance. The quantity calculating system may additionally comprise the substance temperature sensor 190 (FIG. 1) for measuring the temperature changes within the substance and the ambient temperature sensor 192 for measuring the ambient temperature.

The initial quantity of the substance contained in the chamber 106 may be known, such as the weight, denoted by "$m_1$". The ambient temperature sensor 192 may be used to measure the initial ambient temperature "$T_{ai}$" while the initial time "$t_i$" is recorded. At the same time, at $t_i$, the substance temperature sensor 190 may measure the initial substance temperature "$T_{si}$".

These measurements may be repeated and recorded until the substance temperature changes by $\Delta T$. In other words, these measurements may be repeated until the current measured substance temperature, $T_s(t)$, has changed from the initial substance temperature, $T_{si}$, by $\Delta T$, such that at a final time "$t_f$" it is established that $T_s(t) - T_{si} = \Delta T$.

In some embodiments, to ensure the ambient temperature is substantially stable and constant during the repeated substance temperature measurement, the ambient temperature is measured and compared to the initial ambient temperature, $T_{ai}$. Whereupon the current ambient temperature $T_a(t)$ is identical or substantially similar to the initial ambient temperature $T_{ai}$ (with some allowed deviation) the respective data generated by the substance measurement $T_s(t)$, $T_{si}$, $\Delta T$, $t_i$ and $t_f$, will be recorded and utilized.

From these time recordings a first time span t, denoted by $t_1$, is found that: $t_1 = t_f - t_i$ which is the time it takes for the substance under constant heat flux to achieve the predetermined temperature change, $\Delta T$ at a first time span.

The substance temperature and ambient temperature measurements may be repeated and the time $t_1$ can further be averaged or recorded for different substantially constant ambient temperatures. The result may be a table or any other form demonstrating an empirical relationship between the time duration, t, it takes to achieve the predetermined substance temperature change, ΔT, at a constant ambient temperature, and a series of constant ambient temperatures.

Following a change in the substance quantity, the measurements may be repeated as described hereinabove and a second time span $t_2$, wherein $t_2=t_f-t_i$ is recorded at a respective constant ambient temperature.

In some embodiments, the recorded times $t_1$ and $t_2$ and the corresponding temperature measurements (e.g. $T_s(t)$, $T_{si}$, ΔT) may be utilized to calculate the substance quantity in any suitable manner. In some embodiments, the averages of $t_1$ and $t_2$ may be calculated and the corresponding temperature measurements may be utilized for calculating the substance quantity, according to the following non-limiting exemplary algorithm or in any other suitable manner:

The amount of energy "Q" required to change the temperature of a substance by the predetermined temperature change ΔT is generally calculated by:

$$Q = mC_p\Delta T \quad \text{Formula 1:}$$

Where m is the substance weight and $C_p$ is the substance specific heat capacity (specific heat).

Since it is established that: Q [joules]=Φ [watts]×t [sec]

The time for a substance to change its temperature by ΔT under constant heat flux Φ may be calculated by $$t = mC_p\Delta T/\Phi \quad \text{Formula 2:}$$

Hence, a change in the substance weight, while the other parameters are constant, will result in a change of time span t it takes to achieve the same change in temperature ΔT.

Whereupon the substance weight is reduced, which occurs following use of the substance, it will take a shorter time span t to achieve the specific temperature change ΔT.

The time span t can be found from $$t_1 = m_1 C_p \Delta T/\Phi, t_2 = m_2 C_p \Delta T/\Phi$$

since $t_2$ shorter than $t_1$ it satisfies $t_2=t_1-\Delta t$ therefore Δt can be expressed as:

$$\Delta t = t_1 - t_2 = (m_1 - m_2) C_p \Delta T/\Phi = \Delta m C_p \Delta T/\Phi$$

The ratio $t_2/t_1$ it is then:

$$t_2/t_1 = (t_1 - \Delta t)/t_1 = 1 - \Delta t/t_1 = 1 - ((\Delta m C_p \Delta T/\Phi) \times (\Phi/m_1 C_p \Delta T)) = 1 - \Delta m/m_1$$

from this: $\Delta m/m_1 = 1 - (t_2/t_1)$ or $$\Delta m = m_1(1-(t_2/t_1)) = m_1((t_1-t_2)/t_1)$$

Or finally $$\Delta m = m1 \frac{\Delta t}{t1},$$

where $\Delta t = t_1 - t_2$

Thus the change in the substance quantity, such as the weight change Δm, may be calculated based on the initial quantity, such as the initial weight $m_1$, and temperature measurements at that time. The substance quantity may further be calculated based on the time span t, it takes to achieve the predetermined change in temperature ΔT, during the initial substance quantity at time span $t_1$ and during a reduced substance quantity at time span $t_2$, This substance quantity calculation may be performed without prior calibration, yet wherein the heat flux can be considered to be constant during the temperature measurements.

In some embodiments, the substance quantity may be calculated according to the above algorithm wherein the net heat flux in the control element 140 can modify the substance temperature by the required temperature change ΔT within a finite time. Therefore a condition for the measurement may include:

$$|Ta-Ts| > \Delta T$$

Where Ta is the ambient temperature and Ts is the substance temperature. This condition may be fulfilled wherein the heat flux is constant during the time span t that it takes for the substance temperature to be modified by ΔT, This same constant heat flux may occur also during the substance temperature change by ΔT. This generally occurs since users may use the substance while there is no immediate change in the ambient temperatures. In practical terms, the time to achieve the ΔT change in the substance temperature, may be longer than the activation time of an active control element (e.g. the heating element 254 or an thermo-electric cooler) which is used to shift the substance temperature back from the current substance temperature $T_s(t)$ to the initial temperature $T_{si}$.

In some embodiments, the constancy of the heat flux Φ may be affected by the thermal insulation 170 of the container 104, by the ambient temperature and by the setting point (e.g. the initial substance temperature $T_{si}$) for activation.

In some embodiments, the design of the electrical components of the rapid heating apparatuses of FIGS. 9-13 may include relatively few electrical components (or no electrical components at all) such as a battery 200, wires, optional heating elements, optional temperature sensor and an optional electrical current flow temperature switch. This design allows positioning of the electrical components in a compact form inside a disposable or reusable apparatus 100 and/or container 104. For single use disposable apparatus 100 and/or container 104, the battery 200 may be separated by thermal insulation 170 from the circuit. While priming the device for use, the thermal insulation 170 may be removed and the battery 200 contacts the circuit activating the heating element 424 or 498 or 254. When the temperature reaches the limit temperature, the electrical current flow to the heating element stops, and is renewed when the temperature drops below the limit. This continues for the predetermined time which is required in order to induce the appropriate temperature change in the drug. In some embodiments, the battery 200 and electrical circuit may be designed in a way that the battery 200 can provide the adequate amount of power to the heating element 424 or 498 or 254 to generate the required amount of heat over time.

In some embodiments, the design of the thermal insulation 170 and thermal flow is in a way that the thermal flow will be directed mostly to the substance. This is important to achieve efficient and fast temperature change without overheating the drug or the surface of the device, which may be in contact with the tissue of the user.

While the thermal insulation 170 and heating element 424 or 254 may be integrated into the container 104 or chamber 106, which may be reusable or disposable, they can also be independent and the container 104 is then inserted into the thermal insulation 170. This can cause thermal contact between the injection device surface to the heating element inside the thermal insulation 170.

According to some embodiments, as seen in FIG. 1, the apparatus 100 and/or the container 104 may be configured for transmitting information from components thereof by wireless or wired communication means 198. The information may be related to the environmental condition of the substance or any other information related to the apparatus 100. In a non-limiting example, sensors or detectors (e.g. sensors 190 and/or 192) may be configured to detect a signal and/or any data relating to the operation or use of the apparatus 100. Such signal/data may be transmitted via the wireless or wired communication means 198 to a tracking or communication device 194, to the central database 196, and/or from the device 194 to the central database 196. The transmission may be performed in any suitable manner, such as wirelessly, via an analog short range communication mode, or a digital communication mode including WIFI or Bluetooth or cellular means, cloud based communication, NFC, or via a wired connection or to any remote device to forward the collected data. In some embodiments the apparatus may include a wireless transponder (transmitter and receiver) Bluetooth, NFC or any other communication means. Communication may be to a cloud based App or to a database or any other data storage and/or processing machine, for example.

Additional examples for transmission may be via a network. The network may comprise, the cloud, a local area network (LAN), a wide area network (WAN), or a global network, for example. The network may be part of, or comprise any suitable networking system, such as the Internet, for example, or Intranet. Generally, the term "Internet" may refer to the worldwide collection of networks, gateways, routers, and computers that use Transmission Control Protocol/Internet Protocol ("TCP/IP") and other packet based protocols to communicate therebetween.

In some embodiments, the device 194 may comprise at least one of a remote device, a computer, a cellular phone, smartphone, a tablet, and/or desktop mobile device. In some embodiments, the device 194 may pair with the apparatus 100 by imaging a LED indicator formed on the apparatus 100 or by any other identification mechanism.

The central database 196 may comprise any suitable device or function for storage of the data and/or analysis thereof. The central database may comprise a processor and/or memory. In a non-limiting example, the central database 196 may comprise at least one of a computer, PC, laptop, tablet, smartphone, media player and other mobile or desktop device.

The data may be used by a physician, caretaker or the user (e.g. patient) to track the administration of the substance, e.g. drug 110. Additionally, the data may be used to alert the user upon deviation from the predetermined environmental condition range or threshold. Additionally, the data may be used to alert the user upon reduction of the efficacy of the drug 110 due to excess heat or any other relevant environmental condition and/or parameter, such as upon passage of the drug expiration date, for example. Moreover, the data may be used to inform the user the time the substance was last used, the quantity of used substance, the last time the container 104 was opened and/or past occurrences of use of the substance. Furthermore, the data may be used to inform the user the next time the substance is to be used and possibly the quantity that needs to be used. The information and alert may be provided in any suitable manner such as by an optical or audial signal.

In some embodiments, the data may be used to monitor delivery of drugs in various geographical locations. For example, whereupon drugs 110 are to be transported to a multiplicity of locations, e.g. by a global health organization, or a pharmaceutical distributor, the data may be used to monitor the location of the drug delivery device, such as by a GPS element provided in the apparatus 100.

In some embodiments, an alert may be transmitted to an appropriate entity in case of an undesired deviation from predetermined environmental conditions or the predetermined location. The alert and/or monitoring may be performed for a single the apparatus 100 and/or container 104 in a single location, or for a plurality of the apparatuses 100 and/or containers 104 in a single location or in a plurality of locations.

In some embodiments, the apparatus 100 may be configured to track the type of substance (e.g. drug 110) placed within the container 104. For example, the apparatus 100 may include a passive electronic ID thereon (e.g., RFID), and an ID reader. Through the communication means 198, the apparatus 100 may be connected by wire or wirelessly via a network to the device 194 and/or to central database 196 to forward the collected data indicative of the substance type.

In some embodiments, the apparatus 100 and/or the container 104 may comprise an identification element. The apparatus 100 may be configured to detect the identification element placed on a container 104. In some embodiments, an apparatus 100 may be configured to operate with a selected commercial brand of container 104. The identification element may be used to allow activation of the apparatus 100 upon identification of the selected container 104.

The identification element may comprise an RFID element, an electrical element, such as a wire or a sensor and/or a mechanical element, such as an activation pin or an identification element comprising a mechanical feature such as the recess 162 formed in the cap 160 configured to match the protrusion 164 protruding from the container 104, as shown in FIG. 5.

Further embodiments of the apparatus 100 may be employed in combination with the features described in the present disclosure. Exemplary embodiments of the apparatus 100 are disclosed in applicant's PCT Publication WO 2016/011207, incorporated herein by reference in its entirety.

Dose Tracking

There is provided according to some embodiments of the present disclosure a device, system and method for reporting and communicating signals indicative of substance use as well as amount of used substance from a prefilled, disposable or reusable, substance delivery device to at least one auxiliary unit for analysis, recording and optionally reporting to other mobile units and/or databases.

There are a variety of prefilled disposable substance delivery devices which are used today. Some of these devices can be used several times before the substance reservoir empties, and then discarded. It is desirable to report use of such devices and amount of substance, which remains in the delivery device or amount of substance, which was used following each use without requiring the user to actively report or record such information. It is also desirable to provide a low cost delivery device with wireless reporting functionalities. It is also desirable to provide a relatively light weight, small sized and simple delivery device. The delivery device may also maintain the familiar user experience while delivering the substance.

Additionally, in some cases before using the delivery device to deliver the substance, the device may be primed by the user by ejecting a small amount of the substance, e.g. equivalent to 1 or 2 units of substance, to release trapped air in the delivery device. The disposed substance may, in some embodiments, be distinguished from the substance which is actually delivered to the user.

Therefore, it is desirable to provide a simple, inexpensive prefilled, disposable or reusable substance delivery device and method which is capable of transmitting wirelessly (or by wired communication) or by broadcasting to a remote auxiliary device for analysis, signals indicative of usage of the substance and/or the amount of substance. Additionally there are provided means to differentiate the amount of substance actually delivered from the amount of substance wasted during priming. The analyzed information can be logged in the auxiliary device along with additional relevant information (such as but not limited to time and date and type of substance and identifier of the substance delivery device) for later download, or the information may be wire or wirelessly transferred to an auxiliary device and/or to a data base.

In some embodiments, the systems, devices and methods of the present disclosure provide, inter alia, the following advantages: (i) a simple and inexpensive solution to transfer data relating to the dose (i.e. amount) of substance delivered by the delivery device to an auxiliary device (ii) initiating communication between the delivery device and the auxiliary device just before the delivery device is set with the appropriate dose and/or just before it is used to deliver the dose in order to minimize errors, (iii) allowing differentiation between substance wasted during priming of the pre-filled substance delivery device to substance actually used (iv) analyzing the received data by the auxiliary device to find the dose set and/or delivered, recording the result along with additional relevant information, such as time and date and delivery device identifiers, in the auxiliary device and transmitting the data to a remote database or other devices by wired connection or wirelessly.

Figure 14:
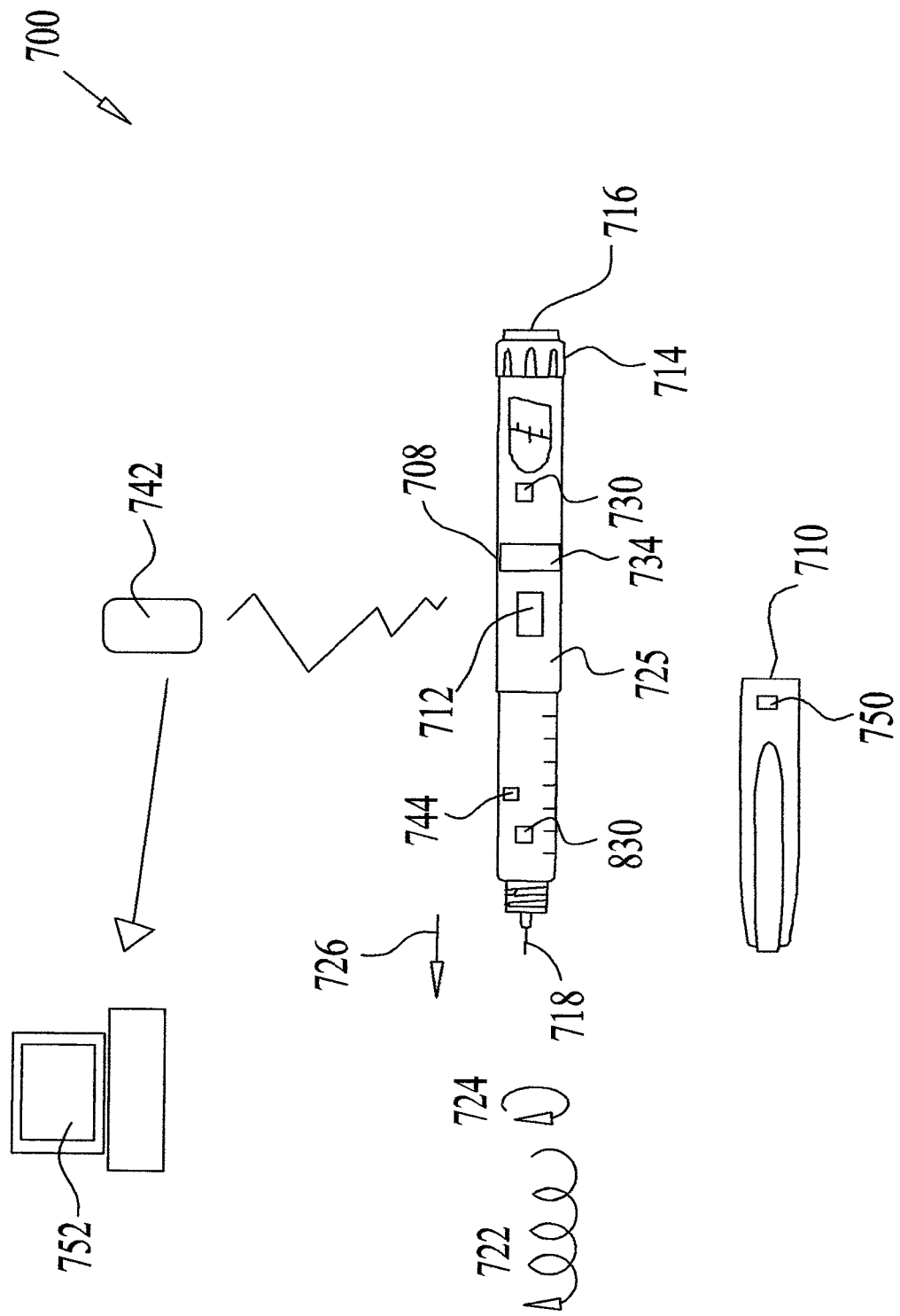
FIG. 14 is a schematic illustration of an exemplary substance delivery system constructed and operative according to some embodiments of the present disclosure.
Figure 15:
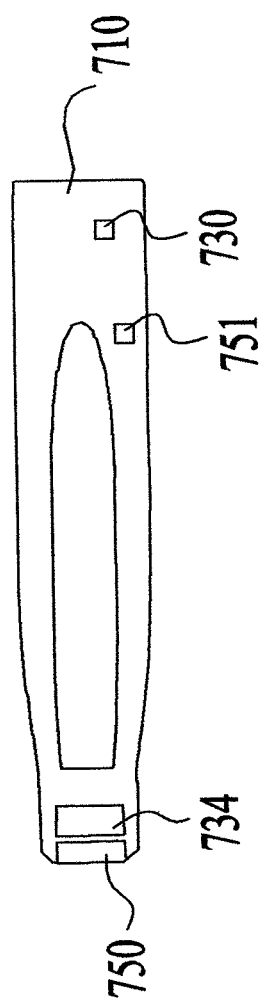
FIG. 15 is a schematic illustration of an exemplary substance delivery system constructed and operative according to some embodiments of the present disclosure.

Referring to FIGS. 14 and 15 which is an exemplary substance delivery system 700, comprising an injection device 708 covered with a cap 710, as shown in FIG. 14 or the substance delivery system 700 may comprise any suitable substance container 104 described in reference to FIGS. 1-13B including a drug delivery device. The injection device 708 may comprise a disposable or reusable prefilled device for example. The description herein may refer to an injection device 708 though the disclosure is applicable to any container 104.

The user may set the desired substance by a dosage selector/delivery element configured to move for propelling a predetermined unit of the substance to exit a reservoir 712 where the substance is contained. The dosage selector/delivery element may be realized by rotating a knob 714, wherein each knob rotation adds an additional substance unit, and thereafter pressing a button 716 which urges the set dose to be delivered to the user via a needle 718.

During setting or delivery of the substance some portions of the delivery system 700 are mobile and some are stationary. The mobile portion may be configured to rotate and advance in a helical orientation shown by arrow 722. In some embodiments the mobile elements rotate clockwise or counterclockwise in the circular orientation shown by arrow 724 (e.g. by turning of the knob 714 in respect to the stationary shaft 725). In some embodiments the elements advance longitudinally in the orientation shown by arrow 726.

In some embodiments, during injection some elements of the injection device 708 are displaced, such as by extension of the shaft 725 towards the skin, and return to their initial position after delivery and in some embodiments element of the injection device 708 are not displaced during injection.

In some embodiments, the delivery system 700 may comprise a sensor 730 or a plurality of sensors 730 configured to detect any suitable signal indicative of the delivery or setting of the substance, such as an audio, visual, pressure and/or vibration signal, for example. The sensor 730 may be positioned in proximity to the signal generation, for example, wherein the detected signal is sound or vibration the sensor 730 may be positioned in proximity to the knob 714 or button 716 generating the sound or vibration. It is noted that such locations may vary between different delivery systems 700 configured with different delivery mechanisms.

The sensor 730 may be a miniature inexpensive sensor. Such inexpensive sensing can be based on sensing the sound and or vibrations or other signals, caused when the injection device 708 is moved to the setting position and or when it is moved to push the substance out for delivery. Integrating the sensor 730 into the delivery system 700 does not alter the user experience of the delivery system 700, which may otherwise occur if the sensor 730 is placed in an additional device accessory to the delivery system 700.

An electronic arrangement 734 may be provided to activate the sensor 730 and transfer the detected signals to a detector positioned at an auxiliary device 742 configured for processing the transferred signal and analysis thereof to determine the dose setting and or dose delivered and/or dose wasted during priming or any other relevant information.

In some embodiments, a transmitting element 744 such as a sonic, ultrasonic or electromagnetic element 744 may be provided to broadcast the detected signal to the auxiliary device 742. The auxiliary device 742 may comprise an auxiliary mobile device such as the cap 710, a blood glucose monitor, smartphone, smartwatch, and other similar devices.

In some embodiments, the electronic arrangement 734 may include at least one resister R, capacitor C and/or inductor L forming a RLC circuit or an RC circuit. Additionally in some embodiments there may be provided one diode and one transistor and at least one switch. A battery 750 may be provided and may be positioned in any suitable location such as in the injection device 708 or on the cap 710 or in the auxiliary device 742.

In some embodiments, such as shown in FIG. 15, the cap 710 may comprise sensor 730, and electronic arrangement 734 (referred to as "electronics"), battery 750 and any other components, thereby the injection device 708 may remain unchanged. The cap 710 may replace a standard, commercial cap of the delivery system 700.

In some embodiments, when the cap 710 is removed from the injection device 708, the cap 710 is usually placed in proximity to the injection device 708 allowing the sensor 730 and electronic 734 to transmit via the transmitting element 744 the detected sensor to the auxiliary device 742. In some embodiments, when the cap 710 is replaced onto the injection device 708 the transmitting element 744 may be configured to cease transmitting.

In some embodiments the cap 710 may comprise a sensor or switch 751 for sensing when the cap 710 is placed on the injection device 708 and when it is removed therefrom.

In some embodiments, the auxiliary device 742 may be used to detect the signal indicative of setting or delivery of the substance, such as the sound and or vibrations and/or other changes which can be sensed and are generated by the injection device 708 when it is set and/or used to deliver the dose. The auxiliary device 742 may commence the detection by either manual activation by the user which switches the device to detection mode, or by automatic recognition which may be based on activity of the user preceding the performance of substance delivery. For example, the auxiliary device 742 may be a blood glucose monitor having built in sound or vibration or other sensor which, following blood glucose measurement, moves to detection mode to identify insulin dose delivered by a prefilled disposable injection device.

Another non-limiting example may be an application running on a mobile device which is activated by the user as part of the substance delivery process wherein sensors in the mobile device or in an accessory connected by wire or wirelessly to the mobile device, detect a signal (sound or otherwise) generated when the delivery device is set for a dose, and or used to deliver a predetermined dose.

In some embodiments, the auxiliary device 742 may comprise the cap 710, which may be reusable or disposable, and may comprise the electronics 734 and power source 750, to detect, analyze, store and optionally transmit by wire or wirelessly the results of detected analyzed signals.

In some embodiments, when the cap 710 is removed from the injection device 708, the cap 710 may be set to a detection mode to detect the signal sensed by sensor 730 and the injection device 708 is set to a transmission mode to transmit the signal to the sensor 730. In some embodiments, when the cap 710 is replaced onto the injection device 708 the detecting and transmitting mode may cease.

The cap 710 may be interrogated at any time by another device (e.g. the auxiliary device 742 or a database 752 in FIG. 14) to provide data stored therein relating to the dose use events (such as date and time, type of substance, a delivery device identifier) and the amount of dose used in each such delivery or priming event. The cap 710 can also include means to detect and control the temperature of the substance contained within the substance delivery device. The system 700 may further comprise any form of passive and or active temperature control (or a combination thereof) like those described herein in reference to FIGS. 1-13B and in described in applicants WO2016011207, applicant's PCT Publication WO 2016/011207, incorporated herein by reference in its entirety.

Figure 16:
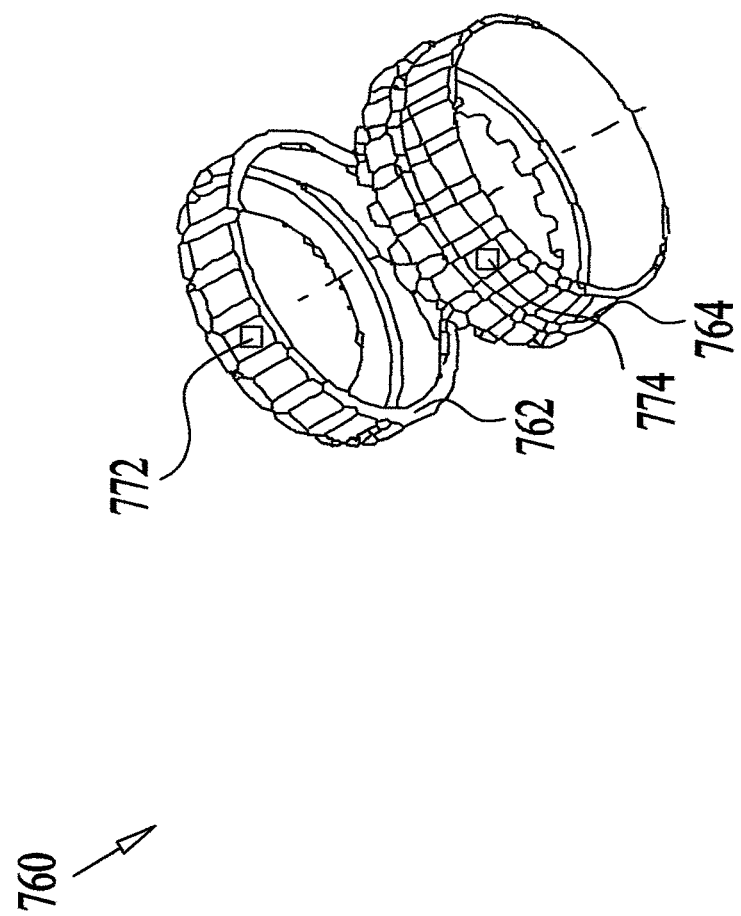
FIG. 16 is a schematic illustration of an exemplary detector assembly used in the substance delivery system constructed and operative according to some embodiments of the present disclosure.
Figure 17A:
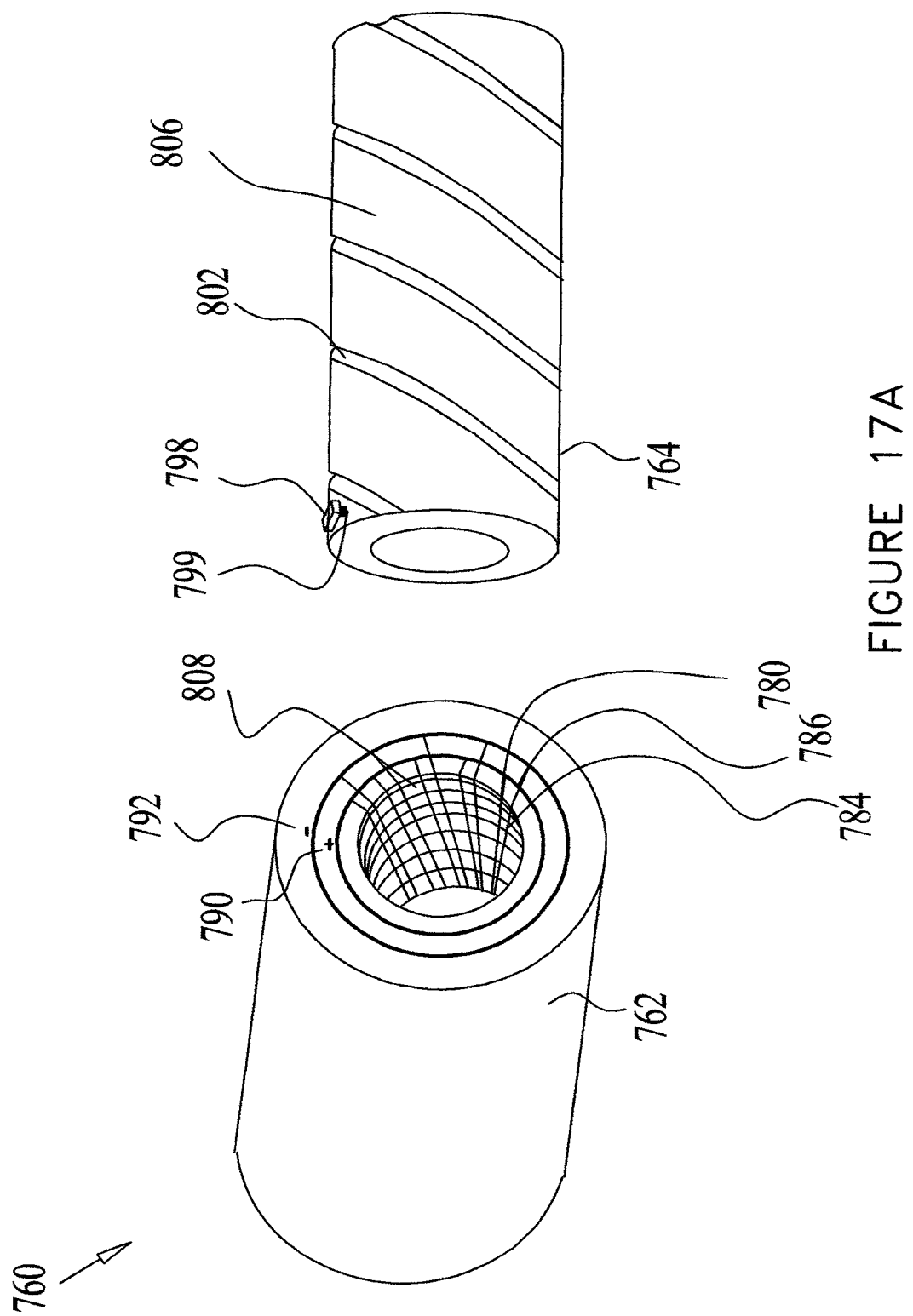
FIG. 17A is a schematic illustration of an exemplary detector assembly used in a substance delivery system constructed and operative according to some embodiments of the present disclosure.

Referring to FIGS. 16 and 17A, according to some embodiments, electronics 734 may be realized by utilizing the stationary and mobile portions of the delivery system 700. The electronics 734 may be positioned on a detector assembly 760 (which may include the senor 730) comprising a stationary portion 762 configured to be positioned on the injection device stationary portion and a mobile portion 764 configured to be positioned on the injection device mobile portion.

The movement of the mobile portion 764 with respect to the stationary portion 762 may be proportional to the set dose and/or delivered dose and/or wasted primed dose. A first electronic element, schematically shown as block 772 may be provided on the stationary portion 762 and as second electronic element 774 may be provided on the mobile portion 764. The first and second electronic elements 772 and 774 may be integrated into the injection device 708 prior to handling by the user or before it reaches the user, such as during manufacturing, or may be inserted therein by the user. The first and second electronic elements 772 and 774 are configured, upon movement of the mobile portion 764 with respect to the stationary portion 762, to generate a signal (e.g. any electromagnetic signal) which can be detected and analyzed to provide information regarding the set dose or delivered or wasted primed dose.

The stationary portion 762 and mobile portion 764 may comprise any combination of stationary and moving parts of the injection device 708. In a non-limiting example the setting knob 716 can be the mobile portion 764 while the shaft 725 can be the stationary portion 762. In some embodiments the stationary portion 762 and mobile portion 764 may be add-on portions placed on stationary and mobile parts of the injection device 708.

Rotation of the setting knob 714 is proportional to the set dose and/or delivered and/or primed wasted dose. The second electronic element 774 on the setting knob 714 interacts with the first electronic element 772 on the shaft 725 to generate a signal, such as an electromagnetic signal which can be detected and analyzed to provide information about the set dose and/or delivered and/or wasted primed dose.

In some embodiments, the first and second electronic elements 772 and 774 may comprise a pair of electromagnetic elements wherein moving one of them with respect to the other generates or modifies an electromagnetic signal. In some embodiments, the first and second electronic elements 772 and 774 may be a single element or a series of similar or varying elements having a predetermined spacing therebetween which is proportional or otherwise corresponds to the unit dose setting of the substance delivery device. Therefore, moving one of the first or second electronic elements 772 and 774 with respect to the other generates an alternating signal with intervals within the pattern of the signal, which correspond to the rotation spacing. Analysis of these signals provides information indicative of the set dose and/or delivered dose and/or the wasted primed dose. A further example is described in reference to FIGS. 17A and 17B.

In some embodiments, the battery 750 (primary or rechargeable) is included within the cap 710 which can be reusable or disposable. A capacitor C is included in the injection device 708. Upon connecting the cap 710 to the injection device 708 contacts from the cap 710 to the injection device 708 allow charging of the capacitor which in turn serves as the power source for activating the electrical components (e.g. a resistor R and inductor L) residing within the injection device 708 when the cap 710 is removed and charging halts, to enable transmission of the electromagnetic signal from the injection device 708.

Figure 20A:
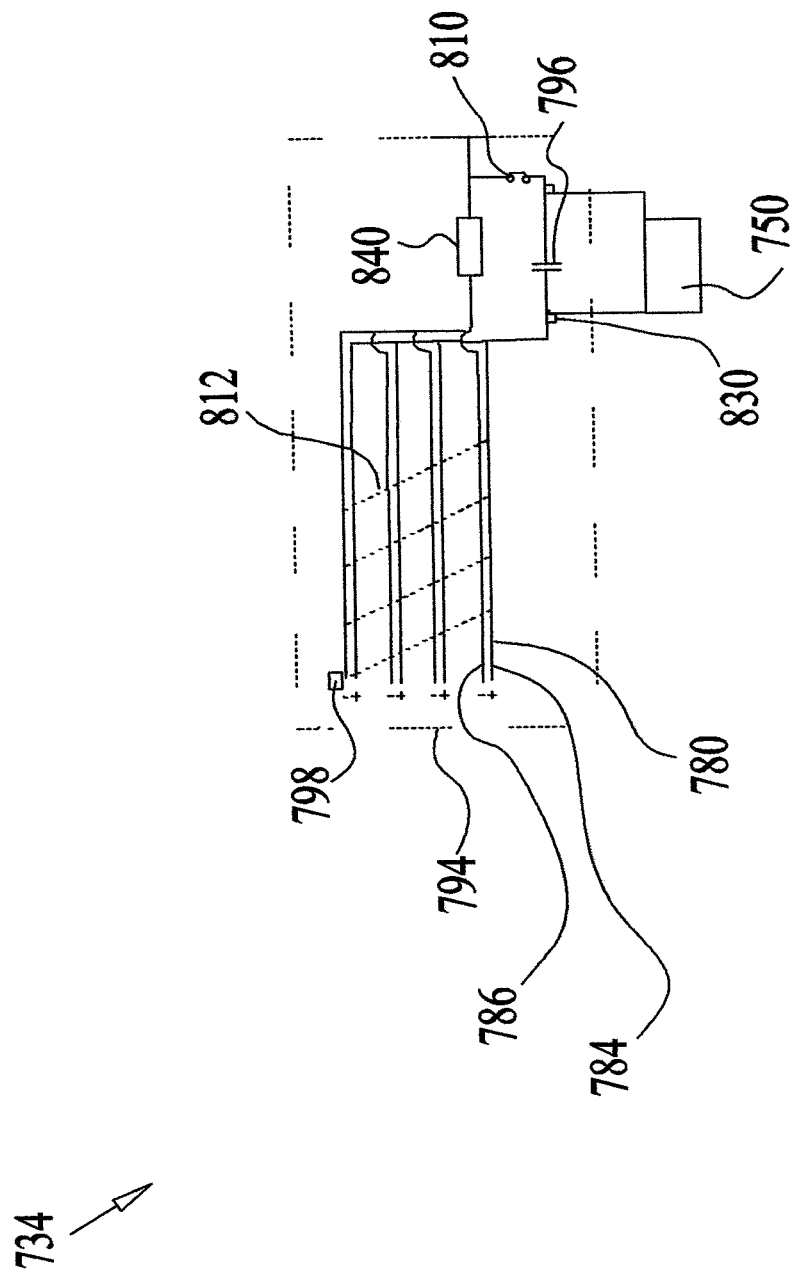
FIGS. 20A and 20B are a each simplified schematic illustration of an electrical circuit of an exemplary transducer, shown at a first operative mode (FIG. 20A) and a second operative mode (FIG. 20B).

Turning to FIG. 17A, the stationary portion 762 and mobile portion 764 may comprise concentrically fitting portions. The mobile portion 764 may be designed to move helically within the stationary portion 762. The electrical components 734 may further comprise electrical conducting wires 780 positioned on the injection device 708, such as on the stationary portion 762 as seen in FIG. 17A, or on the mobile portion 764. The conducting wires 780 may be formed as a plurality of pairs of wires. Each pair has one positive contact 784 and one negative contact 786. The positive contacts 784 are connected at one end to the positive termination port 790, and the negative contacts 786 are connected at another end to the negative termination port 792. The positive and negative termination ports 790 and 792, respectively, are part of an electrical circuit 794 (FIGS. 20A and 20B) of the electronic components 734 provided to generate an electronic signal when the parts of the electronic circuit form a close circuit. The circuit 794 may include a current source, such as a battery 750 or a charged capacitor 796 (FIG. 20A).

A resistor 798 with brush-like contacts (e.g. two contacts) 799 is provided on the mobile portion 764 (or may be on the stationary portion 762) and is configured to engage and disengage the conducting wires 780 as the mobile portion 764 moves in respect to stationary portion 762. The engagement and disengagement create an alternating signal 800

(FIG. 17B) with intervals corresponding to the relative movement between the mobile portion 764 and the stationary portion 762.

The mobile portion 764 may be formed as a cylinder or any suitable configuration for moving in respect to a bore formed within the stationary portion 762 while contacting the resistor 798 with the conducting wires 780. The mobile portion 764 may be formed with helical grooves 802 and is configured to move in a helical orientation 722 within the stationary portion 762. The pitch 806 of the grooves 802 may be designed to correspond to the movement caused by the dosage selector/delivery element. For example, the distance between each turn of the knob 714 may correspond or may be equal to pitch 806.

The resistor 798 with two (or one or more than two) brush electrical contacts 799 may be sized to fit or be slightly larger than the space between the pairs of conducting wires 780 yet smaller than the pitch between the conducting wires 780. Thus as the brush contacts 799 of resistor 798 helically rotate within the stationary portion 762 the brush contacts of the resistor 798 engage and contacts the conducting wires 780, thereby closing the electric circuit 794. The closed circuit generates the signal 800 configured to correspond with the resistor value. As the mobile portion 764 further advances to the gap 808 between the pairs of conducting wires 780, the brush contacts 799 of the resistor 798 disengage and disconnect with the conducting wires 780, thereby opening the electric circuit 794 and ceasing the signal generation.

Therefore, the helical movement of the mobile portion 764 within the stationary portion 762 generates an alternating "on and off" signal. As seen in FIG. 17B the peaks represent the signal 800 generated upon closing the electric circuit 794. The number of signal 800 correspond to amount the substance units which were set and/or delivered and/or wasted during priming.

The alternating electronic signal 800 may be transmitted wirelessly or by a wired connection to the auxiliary device 742 to be analyzed, recorded, and optionally transmitted to a remote database 752.

It is appreciated that the alternating electric signal 800 may be generated by electrically engaging and disengaging any of at least two portions of the system 700.

Figure 20B:
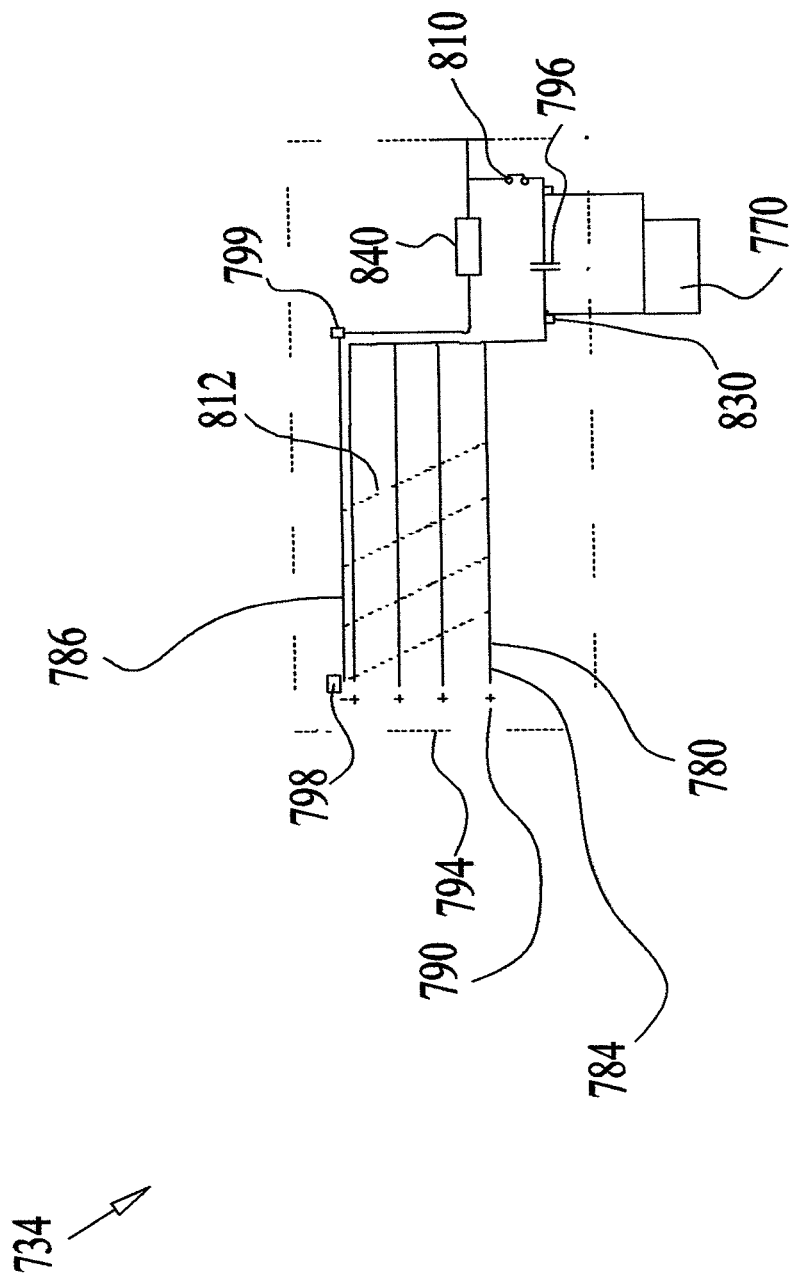

In some embodiments, the electrical circuit 794 comprises an optional electrical push switch 810 (FIGS. 20A and 20B). The push switch 810 may be located at or in proximity to button 716 such that upon pressing the button 716 for delivery of the substance the mobile portion 764 advances in the orientation of arrow 726 (FIG. 14) causing the push switch 810 to contact the contacting wires 780 which closes the push switch 810. This closed push switch 810 closes the circuit 794 which generates the electrical signal 800. This electrical signal 800 is generated due to pressing button 716 and thus is indicative of the substance delivery.

In some embodiments the electric circuit 794 comprises a capacitor 796 charged by a battery 750, which may be placed in any suitable location such as on cap 710. Upon removing the cap 710 from the injection device 708, generally prior to use of the injection device 708, the capacitor 796 provides electrical power to the electrical circuit 794. The exemplary electrical circuitry is shown in FIG. 20A.

In some embodiments, as further shown in the exemplary electrical circuitry of FIG. 20B. The resistor 798 comprises a termination port of one electric wire of one polarity (for example the positive termination port 790) on the surface of the mobile portion 764. A brush contact 799 at the other end of that electrical wire is in contact with a contact wire of the same polarity on the inner surface of stationary portion 762. The second polarity wire (the negative in this example) divides to several wires with a gap therebetween that is on the inner surface of the stationary portion 762 along the wire of movement of the mobile portion 764, which helically moves along the inner surface of the stationary portion 762 upon delivery of the dose or setting of the dose or priming.

Movement of the moving portion 764 engages the resistor 798 with the contact wire 780 of the opposite polarity whenever it meets the wire 780 of the opposite polarity on the surface of the stationary portion 762. This closes the electrical circuit 794 and generates a signal 800. When the resistor 798 is removed from the wire 780 the signal ceases to be generated. In this example whenever the moving portion 764 moves in a helical orientation 722 along the stationary portion 764 the resistor 798 on the surface of the moving portion 764 comes in contact and disengages from the contact wire 780 on the inner surface of the stationary part. Therefore, the helical movement of the rotating, mobile portion 764 around and along the inner section of the stationary portion 762, which is along the shaft 725, generates the alternating "on and off" signal 800.

In this example, with number of "on" values that correspond to the number of times the rotating moving resistor 798 closed the circuit 794 while it moves on the mobile portion 764 is shown by peaks 800 in FIG. 17B. As the gap 808 between the wires 780 is designed to correspond to the dislocation on the injection device 708 during setting each substance unit, the number of detected signals 800 correspond to the amount of substance units that were set and/or delivered and/or wasted during priming.

In some embodiments, the elements on the stationary and moving portions 762 and 764 are encoded with encoding that is transmitted by the injection device 708, to allow distinction between different injection devices 708 transmitting to the same auxiliary unit 742, allowing it to identify whether a total dose is detected from a single injection device 708 or is the dose an accumulation of doses set in a plurality of injection devices 708.

In some embodiments, the value of the resistor 798 can be designed to be different for different systems 700 to allow distinction between different injection devices 708.

Referring to FIG. 17B, at the left side graph the dotted line 812 indicate the helical movement of the resistor 798 along contact wires 780, including the pairs of positive wires 784 and negative wires 786.

The resultants electrical signal 800 generated upon contact of the resistor 798 with the contact wires 780 while advancing of the mobile portion 762 within the helical path of the stationary portion 764 is shown at the right side graph.

The spacing between each positive wire 784 and negative wire 786 is shown to be smaller than the spacing between each pair of wires 780.

In some embodiments the electrical arrangement 734 may comprise further components, such as additional resisters 798, for example.

Figure 18:
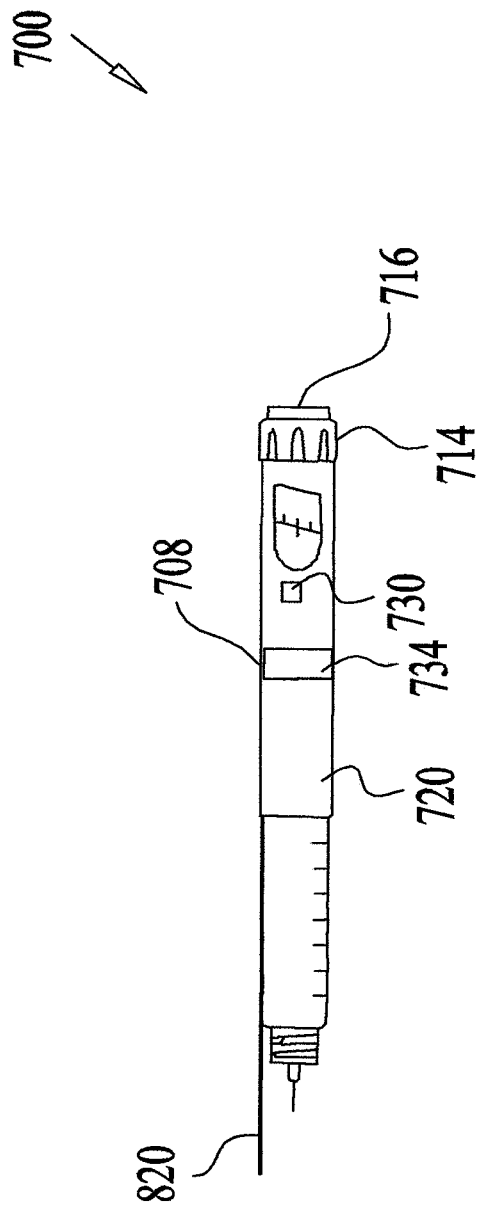
FIG. 18 is a schematic illustration of an exemplary substance delivery system constructed and operative according to some embodiments of the present disclosure.
Figure 19:
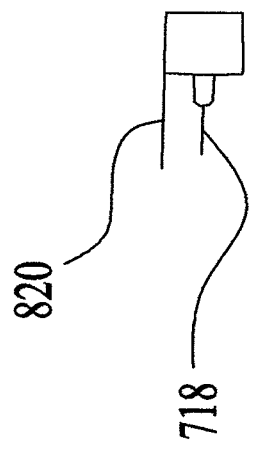
FIG. 19 is a schematic illustration of an exemplary substance delivery system constructed and operative according to some embodiments of the present disclosure.

Referring to FIGS. 18 and 19 it is seen that in some embodiments the injection device 708 (FIG. 18) or the needle portion 718 (FIG. 19) may include a touch wire 820 extending therefrom. The touch wire 820 is configured to contact the electronic components of the injection device 708. The touch wire 820 may be formed at its edge or at any other location, an electrical components sensitive to touching of the skin. Accordingly, upon detecting the electrical signal 800 indicative of the dose, the touch wire may be used to detect touching of the user's skin, thereby allowing distinction between actual delivery of the dose, wherein the touch wire touches the skin, and wherein the dose was set or primed and the touch wire 820 does not contact the user skin. The touch wire 820 may comprise capacitance, impedance, pressure, and/or temperature sensing functionalities to detect skin touch.

The touch wire 820 may be formed at least partially of an electrically conducting and flexible material so it may bend and touch the skin during piercing the skin with the needle 718, for example.

The detection of skin piercing may be performed in any suitable manner, for example, and ultrasonic transponder 830 (e.g. a transmitter and receiver) is used to detect the piercing of the skin by the needle 718. The ultrasonic receiver detects the skin piercing which reflects the ultrasonic signal emitted by the transmitter. The transmitter may be partially or fully placed on the injection device 708. The transmitter can be realized by mechanical moving elements which are designed to generate ultrasonic signals as they move when the dose is delivered. The receiver detects the reflected ultrasonic signal which is indicative of delivering the dose to the user and can thus indicate whether actual dose delivery occurred or setting or priming of the injection device 708 occurred.

In some embodiments, the auxiliary device 742 may execute an algorithm provided for distinguishing between dose delivery and priming. Typically during priming 1 or 2 units are wasted. The delivered dose may be 1 or 2, units and may be larger than 2 units. Whereupon the electrical signal 800, indicative of the number of units, is generated once or twice and after a passage of a some time (e.g. less than 1 minutes or a few minutes) if additional signals 800 are detected, this may indicate that the first 1 or 2 units were wasted during priming and after the time passage the units were delivered. Thus the first 1 or 2 signals 800 may be subtracted from the total number of signals 800 to reflect the amount of delivered dose excluding the wasted primed dose.

Similarly, whereupon the electrical signal 800 is generated once or twice and after a passage of a relatively long time (e.g. more than 10 minutes) no additional signals 800 are detected, this may indicate that the first 1 or 2 units were not for priming rather for actual dose delivery. Thus the first 1 or 2 signals 800 may be indicative of the amount of delivered dose.

In other words, there is provided a method for distinguishing between dose delivery and priming comprising: detecting a first and/or second electrical signal; measuring the duration between the first or second signals and a third signal, whereupon if the duration is equal or less than a predetermined duration than the first or second signal are indicative of a primed dose; and if the duration is more than the predetermined duration than the first or second signal are indicative of a delivered dose.

Referring to FIGS. 20A and 20B there is shown an exemplary elm; Ionic arrangement 734 of the electrical circuit 794 comprising the capacitor 796 charged when a cap 710 is placed over the injection device 708 and used to generate the electromagnetic signal 800 when the cap is off. The switch 810 is pressed and the resistor 798 moves along the pairs of the electrical contact wires 780. The circuit further comprises detectable contacts 830 connecting the cap 710 to the injection device 708 and further optional electrical components 840.

FIG. 20B is a non-limiting electrical layout of an electric circuit having a capacitor 796 charged when the cap 710 is placed over the injection device 708 and used to generate the electromagnetic signal 800 when the cap 710 is off. The switch 810 is pressed and the resistor which is a termination port (790 or 792) of one electrical wires (positive 784 or negative 786) moves along the electrical contact wires 780 of the other polarity.

It is noted in reference to FIGS. 14-20A, that the mobile portion 764 and stationary portion 762 may comprise any 2 or more portions. The portions may both be mobile as one mobile portion moves in respect to another mobile portion.

The mobile portion 764 and stationary portion 762 may comprise any suitable configuration and may comprise any components which upon contacting the other may generate a signal due to the movement of one of the portions. In FIGS. 14-20B electrical contacts were described yet any time of contact, such as chemical or mechanical contact may be made which may generate a signal indicative of the set dose and/or delivered dose and/or wasted primed dose.

In some embodiments, the auxiliary device 742 may comprise the communication device 194 (FIG. 1) and the database 752 may comprise the database 196

While the disclosure has been described with respect to a limited number of embodiment, it is to be realized that any combination of embodiments in whole or part can also be used and that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
an environmental control element configured to control at least one environmental condition of a substance,
a substance chamber configured to contain the substance, wherein:
the environmental control element includes a thermal insulator configured to provide a thermal shield for the substance, and a phase change material (PCM) configured to thermally regulate the at least one environmental condition;
and
a wall configured to surround the substance chamber and comprising a thermally conductive element, and being positioned at least partially in contact with the substance chamber and the PCM;
wherein:
the environmental control element is configured to control the at least one environmental condition without use of an external power source,
the apparatus further comprises a control capacity indicator configured to display a remaining environmental condition control capability provided by the PCM, and
the PCM is configured to change from a first phase to a second phase, and the displayed remaining environmental condition control capability is calculated based on a remaining amount of PCM in the first or second phase.

2. The apparatus according to claim 1, further comprising an enclosure shaped and sized so as to receive the substance chamber.

3. The apparatus according to claim 1, wherein a volume of the PCM exceeds a volume of the substance chamber.

4. The apparatus according to claim 1, wherein the thermal insulator comprises an insulating enclosure formed of two oppositely facing walls and an evacuated gap defined in between the walls.

5. The apparatus according to claim 4, wherein the thermal insulator is formed of two mutually insertable inner and outer insulating enclosures.

6. The apparatus according to claim 5, wherein the PCM is positioned intermediate the inner and outer insulating enclosures.

7. An apparatus according to claim 1, wherein the substance chamber is placed in a pump and the delivery of the substance is by infusion.

8. The apparatus according to claim 1, wherein the control capacity indicator is configured to display a measure of time indicative of the remaining environmental condition control capability.

9. The apparatus according to claim 1, wherein the PCM includes at least two types of PCMs each characterized by a different phase change temperature.

10. The apparatus according to claim 9, wherein the at least two types of PCMs are mixed together.

11. The apparatus according to claim 9, wherein each type of PCM is in layer form and a first type of PCM layer overlies a second type of PCM layer.

12. The apparatus according to claim 1, further comprising a heating element configured to rapidly heat the substance.

13. The apparatus according to claim 12, wherein the heating element is configured to rapidly heat the substance from a temperature in the range of about 2-8° C. to a temperature of around 25° C., within less than 60 seconds.

14. The apparatus according to claim 12, wherein the heating element is configured to rapidly heat the substance from a low storage temperature to a higher use temperature.

15. The apparatus according to claim 12, wherein the heating element is configured to rapidly heat the substance while not exceeding a maximal temperature efficacy limit of the substance.

16. The apparatus according to claim 1, wherein changes in a temperature of the substance temperature are used to quantify the amount of substance in the chamber.

17. A system according to claim 1 further comprising a touch wire configured to detect touching of the skin during dose delivery, thereby providing an additional signal indicative of dose delivery for distinguishing the dose delivery from the dose setting or dose priming.

18. An apparatus comprising:
an environmental control element configured to control at least one environmental condition of a substance,
a substance chamber configured to contain the substance, wherein:
the environmental control element includes a thermal insulator configured to provide a thermal shield for the substance, and a phase change material (PCM) configured to thermally regulate the at least one environmental condition;
and
a wall configured to surround the substance chamber and comprising a thermally conductive element, and being positioned at least partially in contact with the substance chamber and the PCM;
wherein:
the environmental control element is configured to control the at least one environmental condition without use of an external power source,
the apparatus further comprises a control capacity indicator configured to display a remaining environmental condition control capability provided by the PCM, the
the PCM is configured to change from a solid phase to a liquid phase, and the displayed remaining environmental condition control capability is calculated based on a remaining amount of PCM in the solid phase.

19. An apparatus, comprising:
an environmental control element configured to control at least one environmental condition of a substance;
a substance chamber configured to contain the substance; wherein:
the environmental control element includes a thermal insulator configured to provide a thermal shield for the substance, and a phase change material (PCM) configured to thermally regulate the at least one environmental condition;
the substance chamber is surrounded by a wall, and the environmental control element is configured to control the at least one environmental condition without use of an external power source,
a controller configured for calculating a remaining thermal control capacity of the apparatus;
a memory device configured for storing information associated with said remaining thermal control capacity to be retrievable by said controller for said calculating; and
a thermal capacity indicator configured to display the remaining thermal control capacity of the apparatus as calculated by the controller, thereby indicating the remaining thermal control capacity of the apparatus.

20. The apparatus according to claim 19, and wherein the indicator displays the time duration remaining until the PCM will transition from solid to liquid.

21. The apparatus according to claim 20, further comprising:
an ambient temperature sensor for detecting a change in the ambient temperature since a previous ambient temperature detection;
a timer for detecting the time passed since the commencement of the operation of the environmental control element; and
the memory device for retrieving a stored time duration indicating the amount of time it takes for raising the PCM of a volume of the PCM, to a selected temperature.

22. The apparatus according to claim 21, wherein the indication of the remaining thermal control capacity of the apparatus is calculated further based on:
determining for a volume of the PCM one or more time durations it takes for raising the PCM temperature of the PCM volume by one or more temperature differences, wherein each temperature difference is configured from a first temperature to a second temperature;
storing the resultant one or more times durations in the memory device;
during operation of the apparatus detecting a change in temperature by the sensor; retrieving from the memory device a stored time duration of the one or more time durations in accordance with the detected change in temperature; and
subtracting from the retrieved time duration a measure of time that passed since the commencement of operation of the apparatus, thereby calculating a remaining time duration for the PCM volume to be raised to the selected temperature, said remaining time duration being at least partially said indication of the remaining thermal control capacity.

\* \* \* \* \*